United States Patent
Sawada

(10) Patent No.: US 11,474,064 B2
(45) Date of Patent: Oct. 18, 2022

(54) SENSOR AND METHOD FOR DETECTING COMBUSTIBLE GAS

(71) Applicant: James Sawada, Edmonton (CA)

(72) Inventor: James Sawada, Edmonton (CA)

(73) Assignee: James Sawada, Edmonton (CA)

(*) Notice: Subject to any disclaimer, the term of this patent is extended or adjusted under 35 U.S.C. 154(b) by 290 days.

(21) Appl. No.: 16/977,799

(22) PCT Filed: Feb. 18, 2019

(86) PCT No.: PCT/CA2019/050194
§ 371 (c)(1),
(2) Date: Sep. 2, 2020

(87) PCT Pub. No.: WO2019/169476
PCT Pub. Date: Sep. 12, 2019

(65) Prior Publication Data
US 2020/0400601 A1 Dec. 24, 2020

Related U.S. Application Data

(60) Provisional application No. 62/638,132, filed on Mar. 3, 2018.

(51) Int. Cl.
*G01N 27/16* (2006.01)
*G01N 33/00* (2006.01)
*G01N 27/414* (2006.01)

(52) U.S. Cl.
CPC ......... *G01N 27/16* (2013.01); *G01N 33/0047* (2013.01); *G01N 27/4141* (2013.01)

(58) Field of Classification Search
CPC ............... G01N 27/16; G01N 27/4141; G01N 33/0047; G01N 33/004
See application file for complete search history.

(56) References Cited

U.S. PATENT DOCUMENTS 4,331,693 A    5/1982   Wojciechowski et al.
4,414,839 A    11/1983  Dilley et al.
(Continued)

FOREIGN PATENT DOCUMENTS

CA    2113664 A1    7/1994
CA    2238920 A1    11/1998
(Continued)

OTHER PUBLICATIONS

Freakley et al., Palladium-tin catalysts for direct synthesis of H2O2 with high selectivity, Catalysis 351: 965-968 (2016).
(Continued)

*Primary Examiner* — Jennifer Wecker
*Assistant Examiner* — Kathryn Elizabeth Limbaugh
(74) *Attorney, Agent, or Firm* — Jeffrey N. Townes; Cozen O'Connor

(57) ABSTRACT

Sensors and methods for detecting combustible gases in a gas mixture are disclosed based on combustion catalyst compositions comprising an amount of a precious metal supported on an ion-exchangeable alkali metal titanate substrate. The sensors and methods are particularly useful for measuring the concentration of combustible gases in low temperature and high humidity conditions. Advantageously, certain embodiments can selectively measure the concentration of select species (e.g. ethylene).

17 Claims, 10 Drawing Sheets

(56) References Cited

U.S. PATENT DOCUMENTS

| | | | |
|---|---|---|---|
| 4,511,455 | A | 4/1985 | Dosch et al. |
| 4,853,202 | A | 8/1989 | Kuznicki |
| 4,929,582 | A | 5/1990 | Dosch et al. |
| 5,177,045 | A | 6/1993 | Anthony et al. |
| 5,461,022 | A | 10/1995 | Dosch et al. |
| 5,591,321 | A | 1/1997 | Pyke |
| 5,804,703 | A | 9/1998 | Wind et al. |
| 6,668,834 | B1 | 12/2003 | Zikria |
| 6,812,780 | B2 | 11/2004 | Yoshida |
| 6,911,180 | B2 | 6/2005 | Miller et al. |
| 7,159,444 | B2 | 1/2007 | Demarest et al. |
| 8,211,586 | B2 | 7/2012 | Nakakubo |
| 8,580,226 | B2 | 11/2013 | Knoll et al. |
| 8,918,289 | B2 | 12/2014 | Watanabe et al. |
| 9,625,406 | B2 | 4/2017 | Zanella, Sr. |
| 9,739,737 | B2 | 8/2017 | Swager et al. |
| 2011/0100090 | A1* | 5/2011 | Zanella, Sr. ........ G01N 33/0073 73/23.31 |

FOREIGN PATENT DOCUMENTS

| | | |
|---|---|---|
| CA | 2426420 A1 | 5/2002 |
| CA | 3035589 A1 | 5/2018 |
| JP | 2012-81458 A | 4/2012 |

OTHER PUBLICATIONS

Du et al., "Palladium-Tin Alloyed Catalysts for the Ethanol Oxidation Reaction in a Alkaline Medium," ACS Catalysis 2:287-297 (2012).

Bond et al., "Oxidation of Carbon Monoxide over Palladium-Tin(IV) Oxide Catalysts: An Example of Spillover Catalysis," J.C.S. Chem. Comm.: 796-797 (1975).

Zagory et al., Modified Atmosphere Packaging of Fresh Produce, Food Technology 42: 70-74 and 76-77 (1988).

Thomas et al., "Principles and Practice of Heterogeneous Catalysis, Second Edition" (2015).

Liotta, Catalytic oxidation of volatile organic compounds on supported noble metals, Applied Catalysis B: Environmental 100: 403-412 (2010).

Yasuda et al., "Low-Temperature Complete Combustion of Volatile Organic Compounds over Novel Pt/CeO2—ZrO2—SnO2/ $\gamma$ -Al2O3 Catalysts," Bull. Chem. Soc. Jpn. 85: 522-526 (2012).

Jiang et al., "Low-Temperature Oxidation of Ethylene over Platinum Nanoparticles Supported on Mesoporous Silica," Angew. Chem. Int. Ed. 52: 6265-6268 (2013).

Li et al., "Efficient Elimination of Trace Ethylene over Nano-Gold Catalyst under Ambient Conditions," Environ. Sci. technol. 42: 8947-8951 (2008).

Ma et al., "Mesoporous Co3O4 and AU/Co3O4 Catalysts for Low-Temperature Oxidation of Trace Ethylene," J. Am. Chem. Soc. 132: 2608-2613 (2010).

Miller et al., "Nanoscale metal oxide-based heterojunctions for gas sensing: A review," Sensors and Actuators B: Chemical 204: 250-272 (2014).

Moseley, "Progress in the development of semiconducting metal oxide gas sensors: a review," Meas. Sci. Technol. 28: 1-15 (2017).

Zhang et al., "Metal-oxide-semiconductor based gas sensors: screening, preparation, and integration," Phys. Chem. Chem. Phys 19: 6313-6329 (2017).

Morrison et al., Semiconductor Gas Sensors, Sensors and Actuators 2: 329-341 (1982).

Shimizu et al., Basic Aspects and Challenges of Semiconductor Gas Sensors, MRS Bulletin: 18-24 (Jun. 1999).

Siroky, Use of the Seebeck effect for sensing flammable gas and vapours, Sensors and Actuators B 17: 13-17 (1993).

Zhang et al., Ethylene Detection Using Nanoporous PtTiO2 Coatings Applied to Magnetoelastic Thick Films, Sensors 2: 331-338 (2002).

Caprioli et al., "Ethylene detection methods in post-harvest technology: A review," Sensors and Actuators B: Chemical 203: 187-196 (2014).

Azad et al., Solid-State Gas Sensors; A Review, J. Electrochem. Soc, 139: 3690-3704 (1992).

Marcinkowska et al., "A new carbon monoxide sensor based on a hydrophobic CO oxidation catalyst," Sensors and Actuators B 5: 91-96 (1991).

Hall et al., "A black platinum catalyst/pyroelectric gas sensor," Ferroelectrics 54: 211-214 (1984).

Schreiter et al., "Functionalized pyroelectric sensors for gas detection," Sensors and Actuators B 119: 255-261 (2006).

Moseley, "Solid state gas sensors," Measurement Science and Technology 8: 223-237 (1997).

Barsan et al., Conduction Model of Metal Oxide Gas Sensors, Journal of Electroceramics 7: 143-167 (2001).

Agarwal et al., SnO2 Nanoparticle-Based Passive Capacitive Sensor for Ethylene Detection, Journal of Nanomaterials 2012: 1-5 (2012).

Giberti et al., Monitoring of ethylene for agro-alimentary applications and compensation of humidity effects, Sensors and Actuators B 103: 272-276 (2004).

Ivanov et al., "Towards a micro-system for monitoring ethylene in warehouses," Sensors and Actuators B 111-112: 63-70 (2005).

Lundstrom et al., "Gas Sensors Based on Catalytic Metal-Gate Field-Effect Devices," Sensors and Actuators 10: 399-421 (1986).

Kaisti, "Detection principles of biological and chemical FET sensors," Biosensors and Bioelectronics 98: 437-448 (2017).

Winquist et al., "Ethylene production from fruits measured by a simple field-effect structure and compared with a gas chromatographic method," Analytica Chimica Acta 231: 93-100 (1990).

Winquist et al., "Thin Metal Film-Oxide-Semiconductor Structures with Temperature-Dependent Sensitivity for Unsaturated Hydrocarbons," Sensors and Actuators 12: 255-261 (1987).

Janata, "Electrochemical Microsensors," Proceedings of the IEEE 91: 864-869 (2003).

Mcaleer et al., "Tin Dioxide Gas Sensors: Use of the Seebeck Effect," Sensors and Actuators 8: 251-257 (1985).

Fanget et al., "Gas sensors based on gravimetric detection—A review," Sensors and Actuators B: 160: 804-821 (2011).

Balachandran et al., "SnO2 capacitive sensor integrated with microstrip patch antenna for passive wireless detection of ethylene gas," Electronics Letters 44 (2008).

Kathirvelan et al., Ethylene detection using TiO2—WO3 composite sensor for fruit ripening applications, Sensor Review 37/2: 147-154 (2017).

Chauhan et al., "Chemiresistive metal-stabilized thiyl radical films as highly selective ethylene sensors," RSC Advances 4: 46787-46790 (2014).

Pattananuwat et al., "Electrochemical Synthesis of Polyaniline as Ethylene Gas Sensor," Advanced Materials Research 93-94: 459-462 (2010).

Kathirveland et al., "Development of Portotype Laboratory Setup for Selective Detection of Ethylene Based on Multiwalled Carbon Nanotubes,"Journal of Sensors 2014: 1-6 (2014).

Nimittrakoolchai et al., "High-yield precipitation synthesis of tungsten oxide platelet particle and its ethylene gas-sensing characteristic," Materials Chemistry and Physics 112: 270-274 (2008).

Pimtong-Ngam et al., Preparation of tungsten oxide-tin oxide nanocomposites and their ethylene sensing characteristics, Sensors and Actuators A 139: 7-11 (2007).

Ahn et al., "Effect of annealing and argon-to-oxygen ration on sputtered SnO2 thin film sensor for ethylene gas detection," Materials Chemistry and Physics 124: 563-568 (2010).

Jadsadapattarakul et al., "Improved selectivity response time and recovery time by [0 1 0] highly preferred-orientation silicalite-1 layer coated on SnO2 thin film sensor for selective ethylene gas detection," Sensors and Actuators B: 144 :73-80 (2010).

Sun et al., "Synthesis and Characterization of ion-Exchangeable Titanante Nanotubes," Chem. Eur. J. 9: 2229-2238 (2003).

Stephens et al., "Hydrous Metal Oxide Ion Exchanges for Preparation of Catalysts for Direct Coal Liquefaction," Ind. Eng. Chem. Prod. Res. Dev. 24: 15-19 (1985).

(56) References Cited

OTHER PUBLICATIONS

Bunker et al., "Chapter 8: Hydrous Sodium Titanate Ion-Exchange Materials for Use as Catalyst Supports," in Characterization and Catalyst Development ACS Symposium Series; Bradley et al., eds., American Chemical Society (1989).
Huang et al., "Low temperature catalytic oxidation of volatile organic compounds: a review," Catalysis Science & Technology 5: 2649-2669 (2015).
Spivey et al., "Complete Catalytic Oxidation of Volatile Organics," Ind. Eng. Chem.. Res. 26: 2165-2180 (1987).
Van de Beld et al., "A kinectic study of the complete oxidation of ethene, propane and their mixtures on a Pd/Al2O3 catalyst," Chemical Engineering and Processing 34: 469-478 (1995).
Xanthopoulou et al., "Nanocatalysts for Low-Temperature Oxidation of CO: Review," Eurasian Chemico-Technological Journal 17: 17-32 (2015).
Yu et al., "PtZn-ETS-2: a Novel Catalyst for Ethane Dehydorgenation," AlChE Journal 61: 4367-4376 (2015).
Masai et al., "Dehydrogenation and hydrogenation Activity of palladium-Tim-Silica and Nickel-Tin-Silica," Journal of Catalysis 50: 419-428 (1977).
Burch, "Platinum-Tin Reforming Catalysts," Journal of Catalysis 71: 348-359 (1981).

\* cited by examiner

SENSOR AND METHOD FOR DETECTING COMBUSTIBLE GAS

CROSS-REFERENCE TO RELATED APPLICATIONS

This application is a 371 National Stage application of International PCT Application No. PCT/CA2019/050194, filed Feb. 18, 2019, and claims priority to U.S. Provisional Patent Application No. 62/638,132, filed Mar. 3, 2018, both of which are incorporated herein by reference in their entirety.

TECHNICAL FIELD

The present invention pertains to combustible gas sensors and methods for detecting combustible gases. In particular, the invention relates to specific combustion catalyst compositions for use in such sensors, methods for measuring concentrations of combustible gas especially in low temperature and high humidity conditions, and methods for selectively measuring ethylene concentration in gas mixtures.

BACKGROUND

The development of new or improved catalysts has, for centuries, been the domain of the experimentalist and the development of most modern catalysts has progressed along empirical lines. Only once a catalyst is discovered to have new or improved function is work undertaken to understand, using the tools of the day, why a particular formulation functions well while other similar formulations may not. Unfortunately, predictions are difficult to draw from such work because theories which were once in vogue with respect to catalyst mechanism are now considered past fashion as new methods of catalyst investigation are developed. While modern computational methods have combined with organometallic materials research to offer some opportunity to custom design catalysts, the ability to design catalysts, a priori, remains largely out of reach.

While perhaps less arcane than it once was, catalyst development remains a largely discovery-based process. While the knowledge base provided by the prior art can help populate a combinatorial chemistry campaign, knowledge of what has been done before does not ensure a successful outcome for any new study. As such, it is generally understood by those skilled in the art that any change in a catalyst formulation that nets a benefit—from the choice of substrate to the conditions used to prepare or condition the catalyst for use—is generally considered novel because the effect of the change(s) could not be reasonably predicted.

Catalytic combustion is a chemical process whereby a combustible species, in the gas phase, is reacted over a solid catalyst to completely oxidize the target molecules. For molecules containing only carbon and hydrogen (hydrocarbons) or molecules containing carbon, hydrogen, and oxygen (such as alcohols, aldehydes, and ketones) the products of catalytic combustion are solely carbon dioxide and water. Catalytic combustion is frequently, but not exclusively, employed in applications where the concentration of the target species is below its lower ignition limit (LEL). When combustible gases are below their LEL then the mixture will not ignite when exposed to an ignition source. At such dilute concentrations, it is more efficient to use catalysts to react, convert, or combust, the target compounds because a catalyst can facilitate complete oxidation of the target species at a temperature significantly lower than the auto-ignition temperature of the molecule which may be as high as 800° C. It is generally desirable to develop catalysts that are capable of facilitating catalytic combustion at the lowest possible temperature in order to reduce the energy costs associated with operating a catalytic combustion system. Complete catalytic combustion of a target species can only occur when oxygen gas ($O_2$) is found in molar stoichiometric excess; a condition which is easily met when the target species is present in trace quantity in air. Even in a reduced-oxygen environment, provided more moles of $O_2$ are present compared to the moles of carbon atoms to be combusted then complete combustion of the target species can be realized.

A major application of catalytic combustion is related to the removal of volatile organic compounds (VOCs) from air. VOCs are predominantly anthropogenic, organic compounds that have a high vapour pressure at ambient temperature. Such compounds can be alcohols, aldehydes, acetates, aromatics (such as benzene, toluene, and xylene) esters, ketones, alkanes, alkenes, and other compounds comprised of carbon, oxygen, hydrogen, and halogens. To simplify the discussion as it relates to low temperature catalytic combustion, ethylene ($C_2H_4$), carbon monoxide (CO), and formaldehyde ($CH_2O$) will be considered VOCs though, formally, some of these species are excluded from the standard definition of such. The sources of emission of such compounds are varied and VOCs and can be generated by plants, the combustion of fossil fuels, paints and coatings, and from construction and consumer products. Catalytic combustion of VOCs typically takes place over a catalyst bed at elevated temperatures where the catalysis temperature can be dictated by the reactivity of the VOC with the catalyst. Catalyst bed operating temperatures in the range of 200 to 450° C. are typical.

An emerging field of application for catalytic combustion is related to the removal of ethylene from air. Ethylene, also called ethene, is an alkene (an unsaturated hydrocarbon) due to the double bond present in its structure. Ethylene is a potent plant hormone and is generally considered to be responsible for directing the aging process of plants. Ethylene is naturally produced by plants to regulate their life cycle and the gas plays a key role in abscission (the loss or dropping of leaves and fruit), flower formation, as well as fruit growth and ripening. Only trace levels of ethylene, measured in single parts-per-million by volume, are required to provoke metabolic changes in plants and their flowers and fruits. Lowering plant metabolism by storing the goods at sub-ambient temperatures (e.g. <30° C.) is a key tactic in the post-harvest handling of fruits and ornamental plants and flowers and can reduce the unwanted production of ethylene.

Beyond refrigeration, modified and controlled atmosphere storage represent other approaches used to control fruit metabolism and to reduce the associated production of ethylene. In both instances the molecular composition of the gas around the produce is changed to alter its metabolism. By reducing $O_2$ levels and increasing $CO_2$ levels the produce can be held in metabolic stasis and have its freshness maintained for longer periods of time. Controlled atmosphere storage requires constant monitoring and maintenance of the target atmospheric composition; a demand that is more suitable for fixed storage facilities. Modified atmosphere storage, however, is generally applied to packaging applications and typically uses polymer films to manage the concentration of $H_2O$, $O_2$ and $CO_2$ within the package while in transit and storage. To avoid triggering an unwanted anaerobic metabolism event some $O_2$ should be maintained in the modified or controlled atmosphere such that the produce can undergo normal respiration. Under most modified or controlled atmosphere conditions a mole fraction of $O_2$ of not less than 1-5% is used (Zagory, et al. Food Technology 42(9) 70-77) and so the mole fraction of oxygen gas in a controlled or modified atmosphere should always exceed that of the ethylene present in the gas.

Catalytic combustion using a heterogeneous catalyst relies on creating a compound that has a suitably strong affinity for the target species. Before reaction can take place the catalyst first needs to adsorb the target gas species; a process which simultaneously binds the target molecule to the surface of the solid and destabilizes the bonding that holds the molecule together. When the adsorbed molecule is destabilized, adsorbed molecular oxygen can migrate from the surface of the catalyst to react with the adsorbed carbon-containing moieties or $O_2$ may impinge on the adsorbed species from the gas phase (Principles and Practice of Heterogeneous Catalysis. Second Edition eds. J. M. Thomas and W. J. Thomas. Wiley-VCH, 2015). The net result of either mechanism is that carbon-carbon bonds are broken and carbon-oxygen bonds are formed. The efficiency and effectiveness of a combustion catalyst will be dictated by how strongly and selectively it can adsorb the target species and how easily it can release the products of reaction; each of these sequential processes typically taking place under the same reaction conditions. The function of a catalyst is generally enhanced at higher temperatures as catalysts display Arrhenius behaviour which makes their reaction rate exponentially dependent on temperature. This exponential dependence makes catalytic combustion at ambient and sub-ambient temperatures challenging. While suitable catalytic activity may be measured at 200° C., the catalyst may not display any measurable activity at a reaction temperature of 30° C. The temperature dependence of any given catalyst will be unique to its composition.

When a stream containing a VOC (including related compounds such as ethylene, CO, and formaldehyde) is comprised of ambient air, then water vapour is likely to exist as an additional, significant component in the gas stream. The water vapour content of a gas stream is variable and the maximum amount of water vapour that can be present is dependent on the temperature and pressure of the gas stream. When the maximal amount of water vapour is reached, the gas is considered to be saturated with water vapour. Lesser amounts of water vapour are, of course, possible and the amount of water vapour in a gas stream is generally expressed in terms of relative humidity (RH). Relative humidity is defined as the ratio (expressed as a percentage) of the amount of water vapour present in the gas divided by the amount of water vapour needed to saturate the gas at the same temperature and pressure. When the temperature of a gas stream containing a fixed quantity of water vapour is raised isobarically then the effective relative humidity of the gas stream will be changed. Air that is 70% RH at 30° C. will have its relative humidity reduced to only 0.2% RH when the stream is heated to 200° C. because the saturation pressure of water rises from 0.0425 bar at 30° C. to 15.5 bar at 200° C. Thus by heating a catalyst bed to temperatures greater than 200° C. the effective relative humidity of the gas passed over the catalyst can be significantly decreased.

The catalytic combustion of VOCs is complicated by the presence of water vapour. The presence of 2 vol % water vapour (equivalent to 85% RH at 20° C.) in a stream containing benzene is known to have a suppressing effect on the activity of a $Pt/TiO_2$ combustion catalyst but the effect can be largely overcome by operating at temperatures of 200° C. and above (Liotta, L F. Applied Catalysis B: Environmental 100 (2010) 403-412). The effect of an equal amount of water vapour on the same catalyst for the catalytic combustion of ethyl acetate was more pronounced but full recovery of the catalyst's activity could be realized by increasing the catalysis temperature by about 50° C. to 300° C. The reasons behind this suppression were contemplated but no definitive mechanism was proposed. Irrespective of the details of any proposed mechanism, the presence of water vapour serves to reduce the activity and/or stability of the combustion catalyst. Thus to maximize the stability and activity of a combustion catalyst in the presence of water vapour the combustion catalyst can be heated to a temperature that mitigates the influence of water vapour or the combustion catalyst needs to be formulated to be tolerant to relevant levels of water vapour. Catalytic combustion of dilute components in humid streams at temperatures below 200° C. is difficult to accomplish because lower reaction temperatures do not favour catalyst activity and the presence of a significant quantity of water vapour in the stream can interfere with catalyst function.

Wojciechowski in U.S. Pat. No. 4,331,693 titled "Method for Storage of Horticultural Products in Freshness" details the preparation of a catalyst stated to be particularly suitable for the catalytic combustion of ethylene. The catalyst comprises platinum supported on alumina and was prepared by impregnating a porous alumina support with a solution containing 0.05 to 0.5 wt % chloroplatinic acid. To remove trace amounts of ethylene from air, the catalyst bed was maintained at a temperature of at least 200° C. for a period of 5 days. The exhaust stream of the catalytic combustor was returned to ambient using an external heat exchanger to avoid escalating the temperature in a sealed fruit chamber. The efficacy of the catalyst for removing ethylene from the recirculated atmosphere around the sealed quantity of fruit was gauged by assessing the quality the treated fruit versus an untreated, control batch. The humidity of the ethylene-containing air stream was not measured but such catalysis temperatures are sufficiently high to largely overcome the influence of any amount of moisture contributed by fruit respiration to the air stream.

For postharvest applications, the need to recirculate the treated (exhaust) air from the catalytic combustor back into the storage environment naturally restricts the exhaust temperature of a catalytic combustion system; a situation which adds complexity and cost to the system. High temperature catalytic combustion systems also require a great deal of energy to heat the catalyst beds but many shipping and storage applications lack sufficient power to drive such devices. These restrictions have driven catalyst development toward compositions capable of reacting ethylene at lower temperatures.

Japanese patent 2012-081458 by Haruta titled "Catalyst Composition for Catalytic Combustion Reaction of Ethylene and Methods for Decomposing Ethylene by Using the Same" details a series of catalysts formulated using Au, Pd, Ir, Pt and Au/Pt mixtures using a range of metal oxide supports. The most active catalyst was a Au/Pt—$Al_2O_3$ catalyst containing 0.5 wt % Au and 5 wt % Pt. This catalyst was capable of converting half of the ethylene in the dry air stream at 47° C. (0.17% ethylene, balance synthetic air). The authors did not humidify the test gas and all tests were carried out using dry gas.

A study by Yasuda, et al (Bull. Chem. Soc. Jpn. Vol 85, No. 4, 522-526 (2012)) titled "Low-Temperature Complete Combustion of Volatile Organic Compounds over Novel $Pt/CeO_2$—$ZrO_2$—$SnO_2/Al_2O_3$ Catalysts" details the preparation and characterization of the catalyst named in the title. Catalyst formulations were tested dynamically using dry gas containing 1 vol % ethylene by raising the temperature and monitoring the amount of ethylene in the product stream. Other metal mixtures were tried but the authors demonstrate that the title formulation, containing 5 wt % Pt, had the highest activity. The authors did not humidify the test gas and all tests were carried out using dry gas.

In a study by Jiang et. al. (Angewandte Chemi Int. Ed. 2013, 52, 6265-6268) titled "Low-Temperature Oxidation of Ethylene over Platinum Nanoparticles Supported on Mesoporous Silica", the authors detail a series of precious metal-loaded materials based on the mesoporous silicate MCM-41. The authors tested a 1% Pt-MCM-41 catalyst over an extended period of time at 25 and 0° C. using dry test gas containing 50 ppmv ethylene. While the removal efficiency of ethylene remained constant at 25° C. for 12 hours, the catalyst efficiency drops after only 2 hours at 0° C. The authors assign this decrease to water accumulation on the surface of the catalyst and demonstrate that the initial activity is restored only if the catalyst is reactivated. The authors did not humidify the test gases and the only water present in the system would be the result of the catalytic combustion of the 50 ppmv ethylene in the test gas stream.

A report by Li, et al (Environ Sci. Technol. 2008, 42, 8947-8951) titled "Efficient Elimination of Trace Ethylene over Nano-Gold Catalyst under Ambient Conditions" details a material comprising gold precipitated on cobalt oxide. The authors used test gases having different concentrations of ethylene to gauge the stability of their catalysts over a period of 60 minutes. The 4% Au—$Co_3O_4$ catalyst was shown to be able to convert ethylene at concentrations between 5-1050 ppmv at 50° C. The performance of the selected catalyst was, however, only stable for 60 minutes using an ethylene feed of 5 ppmv. At 50 ppm and 1050 ppmv the activity of the catalyst decreases immediately and progressively over the course of 60 minutes; the rapidity of decline being proportional to the ethylene concentration in the feed gas. The authors did not humidify the test gas and so all tests were carried out using dry gas.

A study published by Ma, et al (J. Am. Chem. Soc. 2010, 132, 2608-2613) titled "Mesoporous $Co_3O_4$ and Au/$Co_3O_4$ Catalysts for Low-Temperature Oxidation of Trace Ethylene" details the precise steps required to prepare specific morphologies of cobalt oxide with and without the presence of gold nanoparticles. The authors provide few details associated with their test protocol. A gain of 2.5 times over the plain substrate is achieved by including gold nanoparticles and the authors report an ethylene conversion, at 0° C., of 76%. The study does not provide the necessary details to understand how the experiments were conducted nor how the conversion values were calculated. The authors did not humidify the test gas and all tests were carried out using dry gas.

In all the prior art above, catalytic combustion of ethylene was accomplished either at high temperature (200° C. or above) or at lower temperatures using gases that were not humidified. No results were disclosed nor discussion presented for catalytic combustion in the presence of humidity at temperatures below 200° C.

The presence of unwanted VOC compounds in air may be intermittent and so it is advantageous to confirm the presence and concentration of unwanted VOC compounds in air before implementing a catalytic combustion system to remove the unwanted VOCs. To determine the presence and concentration of a VOC in humid air some method of gas detection or, equivalently, gas sensing is required. A wide variety of gas sensors has been developed with each type having a unique combination of sensor selectivity, response, limit of detection, cost, size, and complexity. The most widely used gas sensors (or detectors) are the so-called solid-state gas detectors because such sensors are deemed to have good response, low limits of detection, low cost, small size, and low complexity.

Solid state gas detectors operate by measuring a property of a solid material that changes when the solid interacts with an analyte gas. Studies by Miller et al.(Sensors and Actuators B 204 (2014) 250-272), Moseley (Meas. Sci. Technol. 28 (2017) 082001), Zhang et al. (Phys. Chem. Chem. Phys. 32017, 19, 6313-6329), Morrison (Sensors and Actuators, 2 (1982) 329-341), Shimizu et al. (MRS Bulletin Jun. 1995 18-24), Siroky (Sensors and Actuators B, 17 (1993) 13-17), and Zhang, et al. (Sensors 2002, 2, 331-338) are incorporated herein by reference and report that the most desirable material for use in a variety of solid state gas sensors is a catalyst and that for the detection of trace amounts of combustible gases in air, the most desirable catalyst is a combustion catalyst.

The prior art demonstrates that gas sensors comprising a combustion catalyst can generally be operated at lower temperatures compared to sensors comprising materials containing no precious metals. Lower temperature operation reduces the energy requirements of the sensor, improves its lifetime, and allows for a greater variety of materials to be used in its construction. The studies also show that sensors will have a higher selectivity when comprised of a combustion catalyst which has a high degree of chemical specificity toward a selected analyte gas. Selectivity is defined as the ability of the sensor to predominately distinguish, in a mixture, a target analyte from amongst other, similar compounds that are present in the mixture. The prior art also establishes that the sensitivity (or limit of detection) of a range of solid state gas sensors is improved when the sensor comprises a combustion catalyst.

In addition to comprising a catalyst, the sensing component of a solid state combustible gas sensor will comprise an internal circuit element, and other circuitry as required, which is selected to measure a property of the catalyst itself or to measure a property of the internal circuit element that changes when an analyte gas interacts with the catalyst. The catalyst is deposited, coated, printed, or otherwise fixed to the internal circuit element so that the catalyst is in intimate contact with the circuit element. The internal circuit element will include electrical connectors which are connected to the internal circuit element and which are located on the outside of the sensing component to allow it to be connected to a suitable external measurement circuit.

A conventional measurement circuit is selected to measure a property of the sensing component in the gas sensor. The measurement circuit generates an electrical signal that relates to the voltage, resistance, conductance, capacitance, flow of current through, or harmonic frequency of, the internal circuit element in the sensing component. Several of these electrical properties can be related to one another through various laws and relationships as are known in the art. One variable can thus be transformed to another by those skilled in the art through the use of appropriate circuitry and electronic instrumentation. A particular measurement circuit may be preferred for a selected sensing component but the selection of a measurement circuit may not necessarily be limiting.

All gas sensors require calibration in order to convert the electrical signals from the measurement circuit into analyte gas concentration values. Calibration is typically accomplished by subjecting the gas sensor to a series of mixtures containing known quantities of analyte gas and recording the response of the measurement circuit for each distinct analyte gas concentration. In principle, the response will be proportional to the reaction rate of the analyte with the catalyst. The rate at which an analyte reacts with the catalyst is governed by the rate constant of the catalyst. The reaction rate constant of the catalyst is exponentially dependent on the working temperature of the catalyst and may also be a function of analyte concentration and relative humidity. The accuracy and stability of the gas sensor will therefore be dependent on whether variations in working temperature, analyte concentration, and humidity will measurably influence the catalyst reaction rate constant when the sensor is in operation.

A combustion catalyst rate constant typically displays Arrhenius behaviour with respect to temperature and so the catalyst rate constant will increase exponentially with increasing temperature. It has been established in the art that the reaction rate of chemical reactions (which include catalytic combustion reactions) will approximately double for every 10° C. rise in temperature. For a reaction taking place at ambient temperature, the normal fluctuations in ambient temperature would be expected to measurably influence the catalyst rate constant. However, at a working temperature between 300-500° C. any fluctuations in the ambient air temperature will not have a measurable effect on the catalyst rate constant. As a result, prior art sensors operating at high temperatures need not correct for the variations in ambient temperature to maintain desirable sensor accuracy.

High levels of humidity are known to have a negative effect on gas sensors comprising combustion catalysts. As stated in a review article by Morrison (Sensors and Actuators, 2 (1982) 329-34) " . . . it is this unfortunate sensitivity of semiconductors to the vapour pressure of water that limits the application of semiconductor gas sensors to high temperature conditions [>300° C.] where physical adsorption of water is minimized." At sufficiently high temperatures (300 to 500° C.), a combustion catalyst is considered to be independent of the normal variations in ambient relative humidity. As a result, prior art sensors operating at high temperatures need not correct for the influence of relative humidity to maintain desirable sensor accuracy.

While the operation of a gas sensor at temperatures between 300-500° C. provides the benefits described above, such sensors have a distinct limitation. Gas sensor operated at such temperatures suffer from cross-sensitivity or an inability to differentiate between similar analytes in a mixture (Shimizu et al. MRS Bulletin Jun. 1995 18-24; Moseley, Meas. Sci. Technol. 28 (2017) 082001; Caprioli, et al. Sensors and Actuators B 203 (2014) 187-196). While ample demonstrations exist for sensors which can detect VOCs at low temperatures, such sensors are limited to either anoxic conditions and/or to gas streams that contain no water vapour.

Numerous types of combustible gas sensors have been developed and the details of their construction and operation have been reported in the art. For instance, pellistor (pellet resistor) types of gas sensors are widely used for sensing and measuring flammable gases in air. The measurement circuit of such sensors makes use of a Wheatstone bridge in which two of the conventional resistor elements are replaced by resistive, temperature-sensing elements. The sensing component for a pellistor sensor comprises both a sensing and reference element. The sensing element comprises a metallic element, such as a wire coil, embedded in or coated with a combustion catalyst. The reference element is comprised of an identical metallic element which is embedded or coated with an inert material. Generally the inert material comprises the same material as used in the catalyst composition but does not contain any precious metals. The sensor and reference elements are placed on opposite sides of the measurement circuit and a voltage potential is applied across them. In a conventional pellistor gas sensor, the gas sensor is designed to allow an amount of electrical current to run through the sensing and reference elements which is suitable to heat the elements to a temperature between 400-500° C. To detect combustible gases in air, both the sensing and reference elements are exposed to the air stream.

When the combustion catalyst in the sensing element is exposed to an air stream containing a combustible gas, the reaction of the combustible gas on the combustion catalyst creates excess heat. This heat is transferred, at least in part, to the metallic element embedded in the combustion catalyst. The heat transferred to the metallic element increases its resistance. The reference element, containing no precious metal, is unreactive toward combustible gases, produces no excess heat, and the resistance of the wire element in the reference element remains unchanged. The difference in resistance between the sensor element and reference element can be measured precisely using an instrument that accurately measures voltage or current.

Pellistor gas sensors have been described in detail by Miller (U.S. Pat. No. 6,668,834), Bristol (U.S. Pat. No. 6,812,780), Demarest (U.S. Pat. No. 7,159,444), Watanabe (U.S. Pat. No. 8,918,289) and Zanella (U.S. Pat. No. 9,625, 406) and are incorporated herein by reference. The high temperature of operation for conventional pellistor gas sensors ensures the activity of the catalyst is not significantly influenced by fluctuations in ambient temperature nor by the presence of varying amounts of water vapour. The high temperature of operation, simultaneously, renders the sensors non-selective because the activity of the catalyst is such that all flammable gases are simultaneously combusted on the catalyst (Azad et al. J. Electrochem. Soc., Vol. 139, No. 12, 3690-3704). As a result, the sensor will not be able to distinguish between different combustible gases in a mixture.

In an alternative design, the same measurement circuit used for a pellistor gas sensor can be adapted to create a thermistor gas sensor. A thermistor (or temperature resistor) is a semiconductor device whose resistance changes as a function of temperature. For a thermistor gas sensor, thermistor elements are used in the sensing and reference elements of the sensing component rather than the metallic elements used in a pellistor gas sensor. It is common, but not essential, to select thermistor elements whose resistance decreases with increasing temperature for temperature measurement applications.

When the combustion catalyst in the sensing element of the thermistor gas sensor is exposed to an air stream containing a combustible gas, the reaction of the combustible gas on the combustion catalyst creates excess heat. This heat is transferred, at least in part, to the thermistor element embedded in combustion catalyst. The heat transferred to the thermistor element changes its resistance. The reference element containing no precious metal, is unreactive toward combustible gases, produces no excess heat, and the resistance of the thermistor in the reference element remains unchanged. The difference in resistance between the sensor and reference elements can be measured precisely using a measurement circuit that measures voltage or current.

Unlike with a conventional pellistor gas sensor, the sensing and reference elements in a thermistor gas sensor are not heated by drawing current through the sensor circuit. When desired, an external source of heat may be used to increase the working temperature of the thermistor gas sensor to any temperature that does not exceed the thermal stability of the thermistor elements (which is typically below about 150° C.). As a result of the temperature limitation of the thermistor temperature sensing devices, thermistor gas sensors are best suited to catalytic combustion reactions that can take place at low temperature. A thermistor gas sensor and its operation has been described by Marcinkowska et al. (Sensors and Actuators B, 5 (1991) 91-96) and is incorporated herein by reference.

Solid state gas sensors can alternatively be designed utilizing the pyroelectric principle. A pyroelectric material such as lead-zirconate-titanate (PZT), by the nature of its crystal structure, generates a voltage across the crystal when it is heated or cooled. Such sensors are typically designed in such a way as to minimize the thermal mass of the sensing component so as to increase the sensitivity and response of the gas sensor. A pyroelectric gas sensing component comprises a thin film or wafer of pyroelectric crystal to whose faces are added a fine coating of conductive material, such as gold. The gold provides a terminal to which an external electrical connection can be made and to which a measurement circuit can be connected. A quantity of combustion catalyst is coated or deposited onto the upper terminal of the pyroelectric crystal which is exposed to the gas stream.

When the combustion catalyst in the sensing component of the pyroelectric gas sensor is exposed to an air stream containing a combustible gas, the reaction of the combustible gas on the combustion catalyst creates excess heat. This heat is transferred, at least in part, to the pyroelectric crystal via the associated conductive metal terminal. The heat transferred to the crystal provokes the crystal to create a transient voltage potential between the terminals. This transient voltage can be measured using a suitable measurement circuit connected to the external electrical connectors. Pyroelectric gas sensors cannot be operated continuously because the voltage produced by the crystal is transient. A pyroelectric gas sensor operates by switching between analyte-free gas and analyte-containing gas. Pyroelectric gas sensors have been described by Hall, et al. (Ferroelectrics 54:1 211-214 (1984)) and Schreiter et al. (Sensors and Actuators B 119 (2006) 255-261) and are incorporated herein by reference.

Chemiresistor or capacitive gas sensors measure an electrical property of a semiconductor which changes in response to a reaction with an analyte gas. Semiconductors distinguish themselves from other materials by having electrical properties that depend on the number of charge carriers present in the bulk or on the surface of the material. These charge carriers can be electrons or they can be "holes" (a vacancy which could be occupied by an electron if one were available to fill it). The field of chemiresistive gas sensors can comprise a range of gas sensing materials including: semiconductor metal oxides (SMO) such as, without limitation, tin dioxide, titanium dioxide, zinc oxide, and mixtures thereof; conductive polymers such as polyaniline and other carbonaceous materials; organometallic complexes; and mixtures thereof. The semiconductor can, advantageously, comprise precious metals in order to promote catalytic reactions on the surface of the semiconductor. Catalytic reactions result in greater changes in electron density on the surface of the semiconductor which increases the sensitivity of the gas sensor. For the detection of combustible gases in air, a combustion catalyst containing precious metal is the most preferred material for use in a chemiresistor gas sensor.

A chemiresistor sensing component, in its simplest form, comprises a pair of terminals embedded in or coated with a semiconductive catalyst. The terminals are typically mounted to an inert, rigid support which may also contain a heating element for heating the sensing component. The reaction of an analyte gas with the catalyst causes electrons to be exchanged between the gas and the solid. The gas can either add or withdraw electrons from the surface of the semiconductor depending on the nature of the semiconductor and analyte gas. Reducing gases such as ethylene, carbon monoxide, and formaldehyde will inject electron density into n-type semiconductors such as, without limitation, tin oxide, titanium oxide, zinc oxide, or mixtures thereof. A chemiresistor sensor component is typically connected, via external electrical connectors attached to the terminals, to a measurement circuit that can accurately measure the resistance, conductance, or capacitance of the sensing component.

When the combustion catalyst in the sensing component of a chemiresistor gas sensor is exposed to an air stream containing a combustible gas, the reaction of the combustible gas on the combustion catalyst transfers electron density onto the surface of the catalyst. This exchange of electrons increases the charge carrier density on the surface of the catalyst. The increase in charge carrier density reduces the electrical resistance of the sensor component which can be sensed between the terminals by a suitable measurement circuit.

Chemiresistor gas sensors have been widely investigated and their construction, properties, and operation have been described in detail by Miller et al. (Sensors and Actuators B 204 (2014) 250-272), Moseley (Meas. Sci. Techol. 8 (1997) 223-237), Moseley (Meas. Sci. Technol. 28 (2017) 082001), Morrison (Sensors and Actuators, 2 (1982) 329-341), Shimizu et al. (MRS Bulletin Jun. 1995 18-24), Barsan et al. (Journal of Electroceramics, 7, 143-167, 2001, Agarwal (Journal of Nanomaterials Vol 2012 Article ID 145406), Pyke (U.S. Pat. No. 5,591,321), Giberti et al. (Sensors and Actuators B 103 (2004) 272-276), and Ivanov et al. (Sensors and Actuators B 111-112 (2005) 63-70) and are incorporated herein by reference.

Another type of gas sensor is the chemical field effect transistor (ChemFET). A ChemFET gas sensor relies on the same semiconductor phenomena that influence chemiresistor gas sensors but a ChemFET gas sensor uses a more sophisticated internal circuit element. A ChemFET sensor circuit is analogous to a MOSFET device (metal oxide semiconductor field effect transistor) whose structure and function is well known to those skilled in the art. A ChemFET sensor circuit uses a semiconductive, gas-sensitive material in place of the $SiO_2$ typically used in a MOSFET device. Again, as with other semiconductor gas sensors, combustion catalysts are the preferred gas-sensitive materials for ChemFET flammable gas sensors (Lundstrom et al. Sensors and Actuators, 10 (1986) 399-421).

A ChemFET sensing component comprises a p-type semiconductor substrate within which are placed two n-doped semiconductor regions. The section between the n-doped regions on the surface of the p-type semiconductor substrate defines the conduction channel A semiconductive catalyst is coated, deposited, or bonded to the surface of the p-type semiconductor and covers the entirety of the conductive channel Terminals are bonded to the two n-doped regions of the p-type substrate, to the surface of the semiconductive, combustion catalyst, and to the bulk of the p-type semiconductor substrate. A potential is applied across the two n-type regions; the negative potential being connected to the "source" terminal (and its associated n-doped region) and the positive potential being connected to the "drain" terminal (and its associated n-doped region). The "gate" terminal (bonded to the surface of the semiconductive combustion catalyst) and the terminal bonded to the bulk of the p-type semiconductor substrate are also connected to the negative potential. ChemFET gas sensors have been described by Kaisti (Biosensors and Bioelectronics 98 (2017) 437-448), Winquist, et al. (Analytica Chimica Acta, 231 (1990) 93-100), Lundstrom et al. (Sensors and Actuators, 10 (1986) 399-421), Winquist at al. (Sensors and Actuators, 12 (1987) 255-261) and Janata (Proceedings of the IEEE, Vol 91, No. 6, 2003) and are incorporated herein by reference.

The voltage potential at the gate electrode controls the conductivity of the ChemFET sensing component. When the gate is at zero voltage the device is intrinsically insulating and no current flows between the source and drain regions across the conductive channel When the combustion catalyst in is exposed to an air stream containing a combustible gas, the reaction of the combustible gas on the combustion catalyst transfers electron density onto the surface of the catalyst. This change in electron density on the catalyst causes a voltage potential to form at the gate terminal. The change in the potential of the gate terminal changes the conductivity of the conductive channel by drawing electrons from the p-type substrate into the conductive channel The change in the conductivity of the circuit element can be measured between the source and drain terminals using a measurement circuit that measures current.

Semiconductor gas sensors have also been developed that utilize the Seebeck, or thermoelectric, effect. The flow of heat through a semiconductor is a phenomenon closely related to the flow of electric charge through the same material. Under conditions where current is prevented from flowing through the measurement circuit, the application of a temperature gradient across a semiconductor will establish a voltage potential. The magnitude of this voltage will be determined by the magnitude of the temperature gradient and the so-called Seebeck coefficient of the semiconductor.

A thermoelectric sensing component can be configured whereby a pair of terminals are placed in intimate contact with the opposite faces of a porous monolith comprising a polycrystalline semiconductive material. One face of the monolith comprises precious metal and functions as a combustion catalyst while the opposite face of the monolith comprises no precious metal. When the combustion catalyst is exposed to an air stream containing a combustible gas, the reaction of the combustible gas on the combustion catalyst creates excess heat. Heat is only generated on the side of the monolith that comprises precious metal and, in this way, a temperature gradient is formed across the monolith which can be sensed between two terminals by a measurement circuit that accurately measures voltage. Such a thermoelectric gas detector is described in detail by McAleer et al. (Sensors and Actuators 8 (1985) 251-257) and is incorporated herein by reference.

A thermoelectric sensing component may be configured to use an external temperature gradient. In such a configuration the sensor component comprises, in addition to two terminals, a support which incorporates a heating element capable of generating a temperature gradient between the terminals. The semiconductive material selected for use in such a sensor circuit is preferred to be a semiconductive combustion catalyst. The applied external temperature gradient establishes a fixed voltage between the terminals. The voltage measured across the terminals, however, is a function of not just the temperature gradient but also the Seebeck coefficient of the semiconductor. The Seebeck coefficient is not constant but varies depending on charge carrier density on the surface of the semiconductor.

When the combustion catalyst is exposed to an air stream containing a combustible gas, the reaction of the combustible gas on the combustion catalyst transfers electron density onto the surface of the catalyst. This exchange of electrons increases the charge carrier density on the surface of the semiconductor. The increase in charge carrier density decreases the Seebeck coefficient of the catalyst. The decrease in Seebeck coefficient can be sensed, by an appropriate measurement circuit, as a reduction in the voltage potential between the terminals Thermoelectric gas sensors of this type have been described by Siroky (Sensors and Actuators B, 17 (1993) 13-17) and are incorporated herein by reference.

Gravimetric gas detectors are yet another type of gas sensor which employ an electromechanical oscillator to which is bonded a gas-sensitive material. When the gas-sensitive material absorbs or adsorbs a gas species, the mass of the oscillator is changed which results in a shift in the resonant frequency of the oscillator. This category of sensors includes bulk acoustic wave (BAW) sensors, surface acoustic wave (SAW) sensors, micro or nanoelectro-mechanical-system (M/NEMS) resonators, capacitive micro-machined ultrasonic transducers (CMUT), and magnetoelastic sensors.

A gravimetric gas sensing component will comprise an electromechanical oscillator (or resonator) to which is bonded a gas-sensitive material. The sensing component will also comprise at least two terminals one of which provides an electrical motive force to the oscillator and the other which transduces or transforms the motion of the oscillator back into electrical signals. A measurement circuit is employed to continuously monitor the resonant frequency of the oscillator which is a function of the input electrical motive force and the mass of the electromechanical oscillator. The resonator can follow a displacement, rotation, or strain motion and the transduction of the motion can be accomplished through capacitive, piezoresistive, or piezoelectric means. For the detection of combustible gases in air, the use of a combustion catalyst (as the gas-sensitive material) in a gravimetric gas sensor component is advantageous (Zhang et al. Sensors 2002, 2, 331-338). It is additionally advantageous if the combustion catalyst need not be heated to elevated temperatures since elevated temperatures can compromise the stability of the oscillator and/or sensor circuit. A comprehensive review of gravimetric gas sensors has been provided by Fanget (Sensors and Actuators B 160 (2011) 804-821) which describes the various forms, features, and functions of the various classes of gravimetric gas sensors and is included herein by reference.

When the combustion catalyst in the sensing component of the gravimetric gas sensor is exposed to an air stream containing a combustible gas, the reaction of the combustible gas on the combustion catalyst is preceded by the adsorption of the gas on the surface of the catalyst. The adsorption of the gas on the combustion catalyst necessarily increases the mass of the combustion catalyst which, in turn, increases the mass of the oscillating portion of the sensor component. This adsorption event is sensed by the measurement circuit, via the terminals, as change in resonant or harmonic frequency of the oscillator. In general, an increase in mass results in a higher resonant frequency.

The calibration of a gas sensor correlates the measured electrical or electromechanical property of the sensor circuit with the concentration of the combustible gas in the air stream. For this purpose, the use of a combustion catalyst in all of the aforementioned sensors is particularly advantageous. When a combustion catalyst reacts with a VOC such as ethylene, carbon monoxide, or formaldehyde several events happen concurrently. The gas first adsorbs on the surface of the catalyst, then undergoes electronic and molecular rearrangement, and finally the products of reaction ($CO_2$, water, and heat) are released. All of the aforementioned gas sensors use a sensing component that is sensitive to one of these events; either the increase in mass of the catalyst, the exchange of electron density with the catalyst, or the generation of heat by the catalyst. The property of the sensing component that is being measured is, in all cases, directly proportional to the reaction rate of the gas with the catalyst comprised in the sensing component.

The reaction rate of the gas with the catalyst will be a function of temperature, relative humidity, and the concentration of the analyte gas in air. In general, more reactions per unit time will occur at higher temperature, lower humidity, and increased analyte concentration. When an VOC is below its LEL the catalyst rate constant can be first order with respect to the concentration of the VOC in air. A first order reaction rate is advantageous for gas sensors because the reaction rate of the VOC with the catalyst will be directly proportional to the concentration of the VOC. That is, if the concentration of the VOC is doubled then the rate of reaction of the gas with the catalyst will be doubled. For a selected working temperature and relative humidity, the aforementioned sensing components will be linearly proportional to the concentration of the VOC in air when the catalyst rate constant is first order with respect to the gas.

Various gas sensors using precious metal based catalysts for the detection of ethylene have been disclosed in the art. For instance, Ivanov et al. (Sensors and Actuators: B 111-112 (2005) 63-70) introduced a series of chemiresistor ethylene sensors based on either $SnO_2$ or $WO_3$. The metal oxides selected were used in their pure form as well as doped with Au, Pt, or Pd. The authors demonstrate that the presence of catalytically-active metals measurably improved the sensor response compared to the same semiconductor that did not have precious metals. Some of the formulations that included a precious metal had a lower sensitivity to humidity than the associated base material. The sensors were characterized at a working temperature between 250 and 450° C. Giberti et al. (Sensors and Actuators B 103 (2004) 272-276) describe a chemiresistor ethylene sensor based on $SnO_2$. The authors explored the effect of impregnating the tin oxide with gold and palladium and concluded that the presence of the precious metal decreased the sensors sensitivity to humidity. The sensors were characterized at a working temperature of 300° C.

Pyke in U.S. Pat. No. 5,591,321 discloses a chemiresistor sensor operating at 50-100° C. which is composed of $Pt/Ir_2O_3$ and/or $Pt/SnO_2$ that can be used to detect combustible gases (including ethylene) produced during an electrical fault in a transformer. It was stated however that the reported sensor could not be used in the presence of oxygen. Dry gases were used in the testing and the influence of water vapour on the sensor was not reported.

Agarwal et al. (Journal of Nanomaterials, Vol. 2012. Article ID 145406) reported an chemiresistor sensor that utilized nanoparticulate $SnO_2$ doped with Pt or Pd. The presence of the precious metals improved the sensitivity of the detector. The reported sensor could detect trace ethylene in the presence of air at a working temperature equal to the room temperature. Dry gases were used in the testing and the influence of water vapour on the semiconductor was not reported.

Zhang, et al. (Sensors 2002, 2, 331-338) reports on a gravimetric sensor that utilized a magnetoelastic thick film coated with Pt—$TiO_2$. The study demonstrated that the incorporation of platinum significantly improved the sensitivity of the sensor. At room temperature, the sensor comprising Pt—$TiO_2$ was shown to be able to detect ethylene at concentrations below 1 ppm. Dry gases were used in the testing and the influence of water vapour on the sensor was not reported.

Various ethylene gas sensors using non-precious metal based catalysts have also been disclosed in the art. For instance, a study published by Balachandran et. al. (Electronics Letters, Vol 44 No. 7 (2008)) detailed the development of a capacitive sensor for ethylene detection. The sensor used pure $SnO_2$. Testing was carried out, presumably, at room temperature and the sensor was demonstrated to be able to detect ethylene in the presence of air. Dry gases were used in the testing and the influence of water vapour on the sensor was not reported.

Kathirvelan, et al. (Sensor Review 37/2 (2017) 147-154) disclosed a sensor based on $TiO_2$-$WO_3$ which was claimed to be able to detect trace amounts of ethylene in air. The working temperature of the sensor was 200-300° C. and the headspace gas mixture from a sample of fruit was used as the source of ethylene. The influence of water vapour on the performance of the sensor was not reported though the operating temperature of the sensor is largely expected to overcome interference effects from water vapour.

Chauhan et al. (RSC Adv. 2014, 4, 46787-46790) reported a chemoresistive sensor using an organometallic structure based on rhenium. The interaction between ethylene and the organometallic complex was stated to be reversible. Testing was carried out in the absence of air using $N_2$ as a balance gas. Dry gases were used in the testing and the influence of water vapour on the sensor was not reported.

Pattananuwat et al. (Advanced Materials Research Vol 93-94 pp 459-462) claimed an ethylene sensor based on polyaniline. The temperature of the testing was not specified but it is expected to have been carried out at ambient temperature. The interaction between ethylene and the polyaniline was stated to be reversible. Testing was carried out in the absence of air using $N_2$ as a balance gas. Dry gases were used in the testing and the influence of water vapour on the sensor was not reported.

Kathirvelan et al. (Journal of Sensors (2014) Article ID 395035) outlined an ethylene detection system that used multiwalled carbon nanotubes. The authors state that the carbon nanotubes reversibly adsorb the ethylene produced by fruit. Testing was carried out at ambient temperature. The authors do not specify that water vapour was present in the test gas streams.

Nimittrakoolchai et al. (Materials Chemistry and Physics 112 (2008) 270-274) reported an ethylene sensor based on a specific morphology of tungsten oxide. Precious metals were not used in its formulation. The response of the sensor toward trace concentrations of ethylene was measured at a working temperature of 300° C. Dry gases were used in the testing and the influence of water vapour on the sensor was not reported.

Pimtong-Ngam et al. (Sensors and Actuators: A 139 (2007) 7-11) disclosed a novel preparation of $WO_3$—$SnO_2$ which could be used to detect ppm-levels of ethylene in a synthetic air mixture. Precious metals were not used in its formulation. The sensor was tested at a working temperature greater than 275° C. Dry gases were used in the testing and the influence of water vapour on the sensor was not reported.

Ahn et al. (Materials Chemistry and Physics 124 (2010) 563-568) disclosed how the ethylene sensing performance of a thin film $SnO_2$ sensor was modified by annealing in various argon/oxygen gas mixtures. Precious metals were not used in the formulation of the active material. The sensor was operated at a working temperature of 300° C. Dry gases were used in the testing and the influence of water vapour on the sensor was not reported.

Jadsadapattarakul et al. (Sensors and Actuators: B 144 (2010) 73-80) reported the improved selectivity of a $SnO_2$ sensor realized by depositing a layer of siliceous zeolite on the surface of the active material. Precious metals were not used in the formulation of the sensor. The authors discovered that the negative influence of water vapour on the sensor was diminished by adding the layer of zeolite to the surface of the tin oxide. Testing was carried out at working temperatures in excess of 250° C.

Dilley in U.S. Pat. No. 4,414,839 reports an n-type semiconductor gas sensor based on $SnO_2$ for detecting trace combustible gases including ethylene. Precious metals were not used in its formulation. The operation temperature of the sensor was not cited and the influence of water vapour on the active material was not discussed.

Swager, et al. in U.S. Pat. No. 9,739,737 reports a chemiresistor sensor that utilizes an organometallic complex tethered to carbon nanotubes. The copper ion in the organometallic complex is purported to reversibly adsorb ethylene. Dry gases were used in the testing except for one result which showed the active material loses 90% of its response to ethylene in the presence of trace (200 ppm) water vapour. $O_2$ was absent and testing was carried out using $N_2$ as a balance gas.

In all the prior art mentioned above, detection of ethylene was accomplished either at high temperature (200° C. or above) or at lower temperatures using gases that were not humidified and/or that did not contain oxygen gas. No results were disclosed nor discussion presented for ethylene detection in the presence of air at temperatures below 200° C. and at a humidity greater than 0.5% RH.

The present invention addresses the need for improved gas sensors capable of detecting and/or measuring the concentration of combustible gases in gas mixtures and particularly in low temperature, humid conditions. In addition, the invention provides other related benefits as will be evident from the following disclosure.

SUMMARY

Combustible gas sensors based on combustion catalyst compositions comprising precious metal supported on an ion-exchangeable alkali metal titanate substrate have been found to be useful in general for detecting and for measuring the concentration of a combustible gas. In particular, such sensors are useful because these combustion catalyst compositions have unexpectedly been found to be acceptably active in low temperature, humid conditions. Further, certain embodiments can be used to selectively measure the concentration of select species, such as ethylene.

Specifically, the invention includes a combustible gas sensor for detecting a combustible gas in a gas mixture. The combustible gas sensor comprises a sensing component and an electrical circuit. The sensing component comprises a combustion catalyst composition comprising an amount of a precious metal supported on an ion-exchangeable alkali metal titanate substrate in which the combustion catalyst composition is exposed to the gas mixture. The sensing component further comprises an internal circuit element in intimate contact with the combustion catalyst composition and external electrical connectors that are electrically connected to the internal circuit element. The electrical circuit of the sensor is connected to the external electrical connectors of the sensing component in order to measure a property of the sensing component, e.g. a property of the combustion catalyst composition or of the internal circuit element.

The alkali metal titanate support in the combustion catalyst composition employed in the combustible gas sensor can be sodium titanate. The precious metal employed can be selected from the group consisting of platinum, palladium, gold and silver. The combustion catalyst composition employed can further comprise an amount of an additional precious metal supported on the ion-exchangeable alkali metal titanate substrate. Further still, the combustion catalyst composition employed can comprise an amount of an additional transition metal on the ion-exchangeable alkali metal titanate substrate. This additional transition metal can, for instance, be zinc, tin, or cobalt. Exemplary combustion catalysts comprise Pt, Pt—Zn, Pt—Sn, Au, Pt—Pd—Sn, Pd, Pd—Zn, Pd—Sn, or Pd—Zn—Sn.

Combustible gas sensors of the invention can be of various types. For instance, the sensor can be a chemiresistor type in which the internal circuit element is a pair of terminals, with the combustion catalyst composition located between the terminals, and in which the measured property is the resistance across the internal circuit element, namely the resistance of the combustion catalyst composition. In a like manner, the sensor can also be another type of sensor, including pellistor, ChemFET, gravimetric, pyroelectric, thermoelectric, or other type. In such embodiments, the internal circuit element can thus be a resistance wire, a thermistor, a field effect transistor, an electromechanical oscillator, or a pyroelectric crystal. And the measured property can thus be the voltage across, the current through, or resistance across the sensing component, the conductance of the sensing component, the capacitance of the sensing component, or the harmonic frequency of the sensing component.

The invention further includes a general method for detecting a combustible gas in a gas mixture comprising oxygen. The method here comprises obtaining the aforementioned combustible gas sensor, exposing the combustion catalyst composition in the sensing component to the gas mixture, and measuring the property of the sensing component. The method can be used to detect combustible gases such as ethylene, formaldehyde, or carbon monoxide. The method is particularly useful for detecting combustible gas in low temperature, humid conditions (i.e. in a gas mixture comprising water vapour). For instance, the method may be used to detect combustible gas in a gas mixture at a temperature below 200° C. and at a relative humidity above 0.5%. The method is also particularly useful for quantitative determination, namely for determining the concentration of the combustible gas from the measured property of the sensing component.

A further advantage of the invention is that it allows for the selective measurement of certain gas species in gas mixtures. For instance, one embodiment of the invention is a method for selectively measuring the concentration of ethylene in a gas mixture comprising ethylene and oxygen. Here, the method comprises obtaining the aforementioned combustible gas sensor, exposing the combustion catalyst composition in the sensing component to the gas mixture, and measuring the property of the sensing component. Again, this method is particularly useful for measuring the concentration of ethylene in low temperature, humid conditions, namely at a temperature below 200° C. and at a relative humidity above 0.5%. As demonstrated in the Examples below, the inventive method can be used to selectively measure ethylene concentration in a gas mixture comprising methane and ethane.

DETAILED DESCRIPTION

Figure 1A:
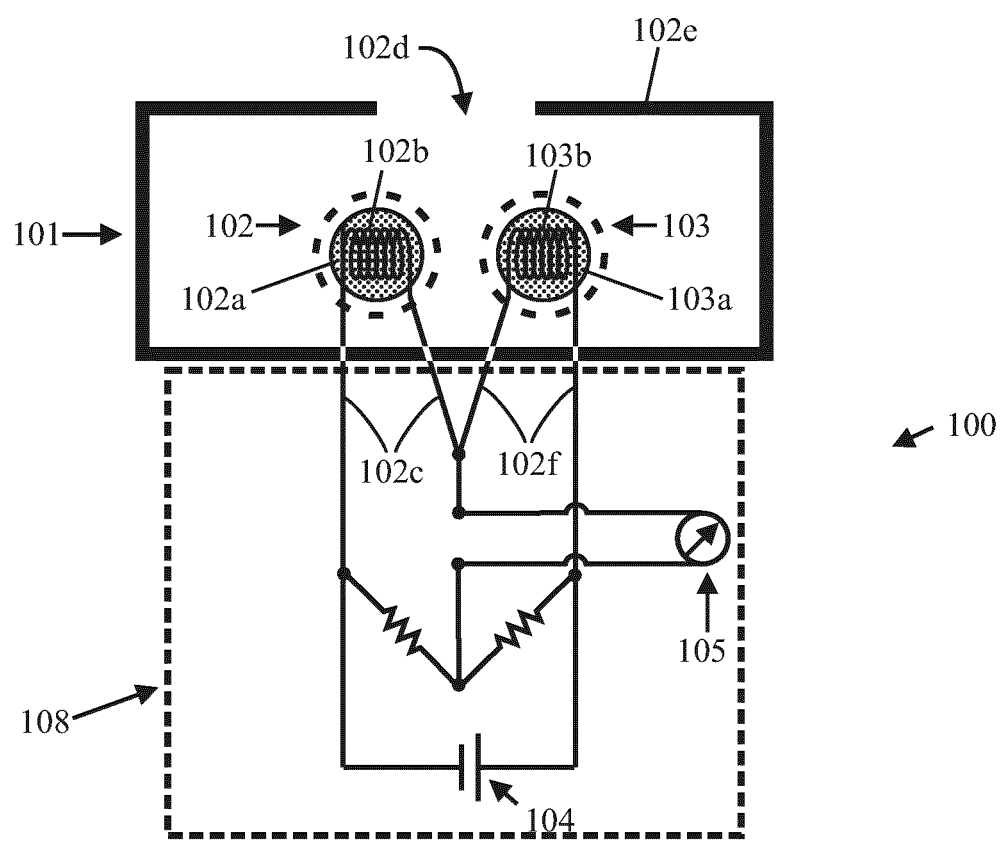
FIG. 1a shows a schematic of a combustible gas sensor of the invention comprising a pellistor type of sensing component and an external electrical circuit. Here, the sensing component employs a reference.

Combustion catalyst compositions comprising precious metal supported on an ion-exchangeable alkali metal titanate substrate have been discovered to be useful for application in combustible gas sensors, particularly because they have unexpectedly been found to be acceptably active in low temperature and high relative humidity conditions. Further, certain compositions have been found to show desired selectivity for important gases such as ethylene A range of gas sensor types and architectures has been developed; all of which can take advantage of such combustion catalyst compositions either to enable or enhance sensor operation. While the power requirements, sensitivity, stability, and response time may be unique to each sensor type, whether or not a gas sensor is able to selectively detect a target analyte in a mixture comprising similar analytes and water vapour will depend on the capabilities of the catalyst selected.

It is well known in the art that a combustible gas will have an activation energy that must be overcome for it to react with a combustion catalyst composition. This activation energy can be overcome most simply by selecting a working temperature suitable for the gas to react. For reactive gases such as ethylene, carbon monoxide, and formaldehyde, this working temperature may be lower than 200° C. However, the working temperature for prior art catalysts is typically fixed to overcome the sensitivity of the catalyst toward water vapour rather than by the activation energy of the analyte of interest. At temperatures where the adsorption of water on the surface of the catalyst is minimized (300-500° C.) the catalysts become indiscriminately reactive and thus the sensor cannot differentiate between similar analytes in a mixture. A combustion catalyst composition capable of operating at lower temperatures and in the presence of a significant amount of water vapour can therefore have enhanced selectivity over prior art catalysts. The field of solid-state gas sensors needs, but hitherto did not have, a combustion catalyst composition which can maintain acceptable activity at low temperature and in the presence of significant levels of humidity.

A combustion catalyst composition that is able to selectively react a target analyte at temperatures below about 200° C. and in the presence of water vapour will circumvent the limitations of the catalysts used in prior art gas sensors. Desirably, the catalyst rate constant of the humidity-tolerant catalyst composition should be independent of the concentration of the analyte in air. It is likewise desirable for the humidity-tolerant catalyst to be reactive toward the analyte at concentrations approaching zero. A sensor incorporating a combustion catalyst composition having these most desirable characteristics would have improved selectivity and sensitivity at low temperature and in humid conditions over prior art gas sensors.

The prior art has demonstrated that by heating a combustion catalyst in a sensor to above of 200° C., trace amounts of organic compounds in humidified air can be detected. The use of such elevated temperatures favours high sensor sensitivity and assists in overcoming the deleterious effect water has on the sensor. However, the use of high temperatures greatly hinders the selectivity of the sensor and such a sensor cannot effectively discriminate between similar combustible gases in a mixture. Since an analyte of interest is rarely the sole combustible component in a mixture, the catalyst should, ideally, selectively react only the target component. In this regard, the detection of trace amounts of ethylene, carbon monoxide, and formaldehyde in air share several common attributes. The presence of the stated contaminants generally occurs within a complex mixture which includes humid air and, in all cases, the quantification of, predominately, a single component in the mixture is desirable. These criteria can desirably be met by integrating, into a gas sensor, a combustion catalyst composition that is able to operate at low working temperatures and that maintains a measurable reaction rate in the presence of water vapour.

The detection of ethylene from the atmosphere around fruits, vegetables, and cut flowers is particularly challenging because, in most cases, the atmosphere around such commodities is refrigerated, maintained at a high RH to preserve produce freshness, and includes a range of other organic compounds produced by perishables as a part of their respiration and ripening cycles. Selectively detecting ethylene from a complex mixture comprising humidity without at least partially separating the mixture into its various components has not yet been accomplished using a solid state gas sensor. If an ethylene-selective sensor could be operated at the ambient temperature of the postharvest transport, storage, or distribution application then such sensors could be operated for long durations on battery power. Such sensors could be incorporated into individual sealed packages of perishables to monitor ethylene concentrations within discrete packages or boxes. A successful combustion catalyst composition for such an application would need to have a measureable reaction rate at ambient and refrigerated temperatures in the presence of significant levels of water vapour.

The need to detect CO in air is driven by the inherent toxicity of the gas toward human health at concentrations as low as 35 ppm. Carbon monoxide occurs in air as the result of the incomplete combustion of organic compounds and is therefore often found in humid air as one component in a complex mixture of other hydrocarbons. Since CO is generally the only toxic component in the mixture the selective detection of this compound is of primary interest. To address this need, solid state gas detectors for CO would benefit from a humidity-tolerant catalyst composition which could be operated at a working temperature whereby CO is predominately combusted on the combustion catalyst.

Formaldehyde accumulation can be an issue in buildings where construction materials are present that outgas the chemical. Without any removal mechanism, the pollutant builds up over time as the air is continuously recirculated through the building. Formaldehyde is toxic at even trace (1 ppm) concentrations and its detection is complicated by the myriad other compounds in air that are present at a similar concentration. To address this need, solid state gas detectors for formaldehyde would benefit from a humidity-tolerant catalyst which could be operated at a working temperature whereby formaldehyde is predominately combusted on the combustion catalyst.

Combustion catalyst compositions appropriate for use in the above applications and in the present invention comprise an amount of a precious metal supported on an ion-exchangeable alkali metal titanate substrate. Such compositions can be prepared by supporting precious metals or mixtures of precious metals and transition metals onto an alkali metal titanate. An alkali metal titanate is an ideal catalyst support due to its combination of high surface area, ion-exchange capability and capacity, and high thermal stability. Herein, an alkali metal titanate is a material which can exchange cations onto the surface of the solid in exchange for the native, alkali metal cations. It is the ability of the alkali metal titanate material to undergo ion exchange at ambient temperature which differentiates an alkali metal titanate from other, unrelated materials, such as barium titanate, which wholly lack this property.

While a range of related materials has been reported in the art, the material subject to the most investigation is sodium titanate; also called hydrous sodium titanate or sodium hydrous titanate. Sodium titanate is exemplary of the alkali metal titanates of the present invention. Sodium titanate is formed by combining a source of alkali—typically sodium hydroxide—with a source of titanium. The source of titanium can be an alkoxy compound such as titanium isopropoxide (U.S. Pat. Nos. 4,511,455; 5,177,045; 5,461,022; 4,929,582) or it can be a source of titanium oxide (U.S. Pat. Nos. 8,580,226; 4,853,202; Sun, et al. Chem. Eur. J. 2003, 9, 2229-2238). In the former cases, the sodium titanate is formed through a precipitation process which can yield X-ray amorphous material while in the latter cases a hydrothermal process is used to convert at least part of the solid titania into sodium titanate and yields a product that displays an identifiable X-ray diffraction pattern. Either process may include additives in the synthesis mixture to promote the formation of specific characteristics in the sodium titanate product. The cation exchange capacity (CEC) of a sodium titanate is typically expressed in terms of milliequivalents per gram of material (meq/g). An equivalent is defined as the number of moles of cations exchanged onto the surface of the titanate multiplied by the valence of those cations. A milliequivalent is simply the product of the number of equivalents multiplied by one thousand. In practice, the cation exchange capacity of a sodium titanate can range (on an as-synthesized basis) between approximately 2 and 6 depending on the quality of material, the cation selected, and the ion exchange conditions used (Sun, et al. Chem. Eur. J. 2003, 9, 2229-2238; Stephens et al., Ind. Eng. Chem. Prod. Res. Dev. 1985, 24, 15-19; Bunker et al Chapter 8, Characterization and Catalyst Development, Bradley et al Editor. ACS Symposium Series Vol 411, 1989).

The choice of precious metal in selecting a combustion catalyst composition is not limiting and platinum, palladium, silver, and gold on a wide range of solid supports have all been shown to be active toward catalytic oxidation reactions. Compositions containing platinum are common for VOC removal applications although palladium and gold-based catalysts have also been broadly explored for catalytic combustion (Liotta, L F. Applied Catalysis B: Environmental 100 (2010) 403-412; Huang, et. al. Catal. Sci. Technol. 2015, 5, 2649-2669; Spivey, J J. Ind. Eng. Chem. Res. 1987, 26, 2165-2180; van de Beld, et. al. Chemical Engineering and Processing 34 (1995) 469-478; Xanthopoulou, et. al. Eurasian Chemico-Technological Journal 17 (2015) 17-32). The use of co-metals in catalyst design is common and bi-metallic and tri-metallic catalyst systems containing both precious metals and transition metals have been applied to high temperature automotive exhaust catalytic combustion applications (Liotta, L F. Applied Catalysis B: Environmental 100 (2010) 403-412; Spivey, J J. Ind. Eng. Chem. Res. 1987, 26, 2165-2180), high temperature hydrogenation/dehydrogenation reactions (Yu, et al. AICHE J. 61: 4367-4376, 2015; Masai, et. al. J. Catal. 50, 419-428 (1977); Burch, R. J. Catal. 71, 348-359 (1981); Freakley, et. al. Science, February 2016 Vol 351 Issue 6276) as well as other selective catalytic oxidation reactions (Du, et. al. ACS Catal. 2012, 2, 287-297; Bond, et. al. JCS Chem. Comm. 1975 796-797). The function of the co-metal may not be precisely known although it has been identified that the co-metal can help prevent the precious metal from sintering at high temperatures or may alloy with the precious metal to alter the electronic environment around the precious metal. Co-metals have also been implicated in facilitating oxygen transport across the surface of the support. Prior art catalyst studies have indicated that certain, lower cost, metals such as zinc and tin, are compatible as co-metals when combined with platinum or palladium. Gold, by contrast, appears to interact positively with cobalt, iron, and nickel. While general observations and inferences can be drawn from the prior art, the selection of precious metal(s) and transition metal(s), their absolute and relative quantities on a support, and the manner in which the catalyst is prepared for reaction remains a matter of discovery for each composition, each type of reaction, and for each set of conditions within a class of reaction.

In the preparation of metal-loaded titanate catalysts it is advantageous, but not essential, to select reagents where the metal salt, in aqueous solution, dissociates to yield a metal cation. Such reagents allow the metals to be deposited onto the surface of the titanate support via an ion-exchange process. Such reagents include tetraammineplatinum (II) nitrate, palladium (II) nitrate, and gold (III) chloride. Tin (II) chloride dihydrate, zinc (II) nitrate, and cobalt (II) chloride also meet this requirement as does Ag (I) nitrate. The reagents may be either anhydrous or hydrated in their crystalline form. Reagent salts that yield metal cations in solution makes it facile to change both the absolute and relative quantities of precious metal and co-metal on the titanate support simply by altering the amount of metal salt dissolved in the ion exchange solution.

It is also possible to formulate titanate catalysts through the process of incipient wetness. The process of preparing a bimetallic titanate catalyst through incipient wetness is provided by Yu, et al. (AICHE J. 61: 4367-4376, 2015). The advantage of using incipient wetness is that reagents can be used where the salt does not dissociate in water to yield a metal cation. The use of incipient wetness impregnation also, advantageously, eliminates filtering as a processing step. It is also possible to prepare titanate catalysts through the process of solid-state ion exchange. The process of solid-state ion exchange can occur when the titanate support is intimately mixed, blended, or ground with a metal salt or salts. When the affinity of the titanate is greater for the metal ion in the salt compared to the ion on the surface of the titanate then a progressive replacement of one for the other can occur through a surface diffusion phenomenon. The process of solid-state ion exchange is typically facilitated by elevated temperatures though the process can occur at temperatures less than half the melting point of the salt; albeit on a longer time-scale.

Such catalyst compositions have been discovered to be acceptable for use in the catalytic combustion of gaseous species in low temperature, humid conditions. The catalyst compositions provide adequate rates of catalytic combustion and, importantly, they remain active when exposed to the species in the presence of elevated levels of water vapour and at temperatures below 200° C. and particularly below 30° C. They are thus especially suitable for use in combustible gas sensors under such conditions.

As mentioned above, there are numerous types or architectures for combustible gas sensors known to those skilled in the art. For instance, there are pellistor, thermistor, chemiresistor/capacitive, ChemFET, pyroelectric, thermoelectric, gravimetric, and other potential types of sensors. What all types have in common is a construction comprising a sensing component which serves to detect a combustible gas in a gas mixture and an electrical circuit connected thereto which measures a changing property of an element within the sensing component. More specifically, the sensing component comprises a combustion catalyst composition, an internal circuit element, and external electrical connectors. In the present invention, the combustion catalyst composition comprises a precious metal supported on an ion-exchangeable alkali metal titanate substrate. The gas sensor is engineered such that the combustion catalyst composition is exposed to the gas mixture to be monitored. The internal circuit element is arranged in intimate contact with the combustion catalyst composition such that the appropriate property may readily be varied and measured as a result of changes in or at the combustion catalyst composition. The external electrical connectors of the sensing component are electrically connected to this internal circuit element in order to provide an electrical connection to the external electrical circuit of the gas sensor. In turn, this external circuit is used to measure the changing signal of the sensing component and hence measure the changing property of the sensing component.

Depending on the sensor type employed, the internal circuit element may simply comprise a pair of terminals with the combustion catalyst composition located at and between the terminals. In such a case, the property measured may be the resistance of the catalyst composition. In other embodiments, the internal circuit element may for instance be a resistance wire, a thermistor, a field effect transistor, an electromechanical oscillator, a pyroelectric crystal, or the like. In other embodiments, the measured property may for instance be the capacitance of the sensing component, the Seebeck coefficient of the sensing component, the harmonic frequency of the sensing component, the voltage across the sensing component, or the like.

The means for integrating the special combustion catalyst compositions into the sensing component are not limited to any method in particular and rather may include any suitable coating or deposition method. The titanate based combustion catalyst compositions could be sol-gel coated, washcoated, dip-coated, printed, drop- or spin-cast, electrosprayed, or mechanically compacted onto or around the internal circuit element in the sensing component. A binder may or may not be used to bond the catalyst composition particles together and to promote adhesion. Additives may be added to the catalyst composition powder that improve the electrical and/or heat conductivity of the coating comprising the titanate combustion catalyst composition. Such additives as may be blended with the powder could include, without limitation, discrete or finely divided carbonaceous materials, finely divided metals, or finely divided semiconductor powders.

Exemplary embodiments of gas sensors of the invention are described in more detail in the following.

Pellistor Embodiment

FIG. 1a shows a schematic of an exemplary combustible gas sensor of the invention based on the typical construction of a pellistor type of flammable gas detector having a sensor circuit based on a Wheatstone bridge. Combustible gas sensor 100 is comprised of sensing component 101 and electrical circuit 108. Sensing component 101 comprises sensor element 102 and reference element 103. In this embodiment, electrical circuit 108 is a Wheatstone bridge circuit which is used to measure the changing resistance of resistance element 102b in sensing element 102. A gas sensor employing a Wheatstone bridge is unique in that it needs both a sensing element and a reference element to function properly and both elements are to be exposed to the same gas stream.

Sensing element 102 comprises combustion catalyst composition 102a that coats or embeds resistance element 102b. Coated/embedded resistance element 102b is housed within an optional insulated housing 102e with external electrical connectors 102c that are electrically connected to opposite ends of resistance element 102b. Insulated housing 102e is open at 102d such that the gas mixture to be monitored has access to combustion catalyst composition 102a therein. Reference element 103 is similar in construction to sensing element 102 but instead comprises inert material 103a, preferably comprising the same material as that of catalyst composition 102a but without precious metals. Inert material 103a coats or embeds resistance element 103b. Insulated housing 102e also has external electrical connectors 102f that are electrically connected to opposite ends of resistance element 103b.

Resistance elements 102b and 103b may be metallic wires, metallic coils, or may be semiconductor devices such as thermistors. Preferably these two resistance elements have equal resistance. Via electrical connectors 102c, 102f, sensing and reference elements 102, 103 connect to and are integrated into a Wheatstone bridge circuit in electrical circuit 108. Potential 104 is placed across the combined sensor and reference elements and Wheatstone bridge. Measurement circuit 105 is used to measure the electrical potential difference between the two branches of the circuit.

Under suitable conditions when a combustible gas encounters combustion catalyst composition 102a in sensing element 102, the combustible gas is catalytically combusted on combustion catalyst composition 102a, but not on inert material 103a. The heat of combustion generated on combustion catalyst composition 102a is transferred, at least in part, to resistance element 102b. The increase in temperature of resistive element 102b changes its resistance. In general, metals increase in resistance with increasing temperature. Thermistor devices, however, may have their resistance increase or decrease with respect to increasing temperature. It is conventional, for temperature sensing applications, to select thermistor devices whose resistance decreases with increasing temperature. Thus, resistance element 102b may conventionally be a thermistor. The difference in resistance between temperature sensing element 102b and 103b causes a potential to develop across the electrical circuit 108 which can be measured by measurement circuit 105 which may be a galvanometer or a voltmeter.

In the present invention, the special low temperature combustion catalyst compositions thus substitute for conventional combustion catalyst compositions in conventional sensing elements in conventional pellistor type gas sensors. Similarly, a quantity of titanate whose composition does not contain precious metals can substitute for the conventional inert material in conventional reference elements in conventional pellistor type gas sensors. The integration of the special humidity-tolerant catalyst into such a gas sensor can improve the selectivity of the gas sensor at working temperatures below 200° C.

Chemiresistor Embodiment

Figure 1B:
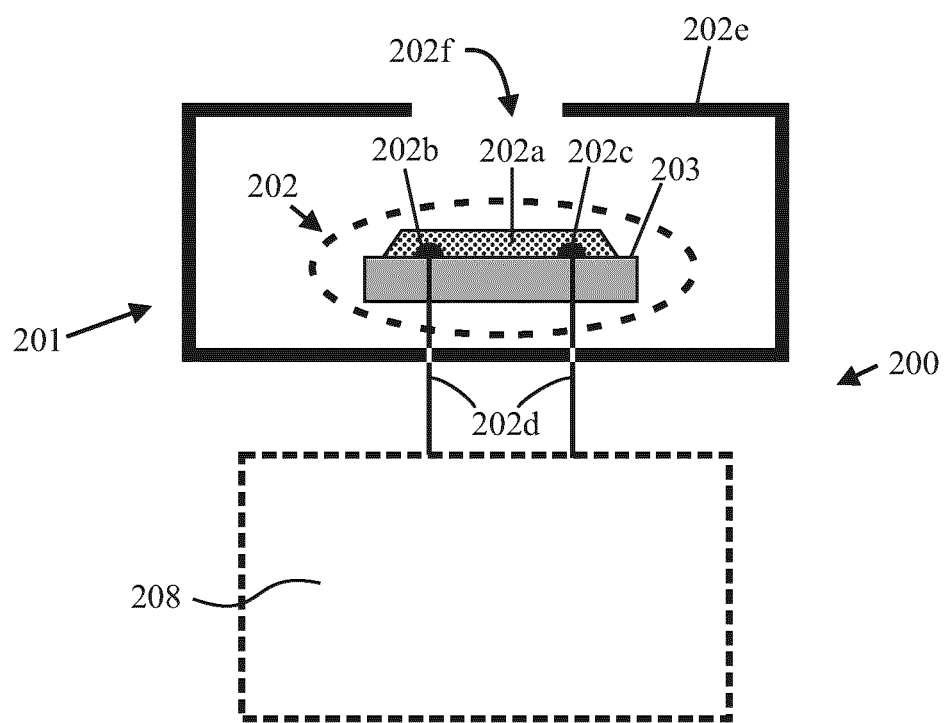
FIG. 1b shows a schematic of a combustible gas sensor of the invention comprising a chemiresistor type of sensing component and an external circuit. Here, the sensing component does not employ a reference.

FIG. 1b shows a schematic of another exemplary combustible gas sensor of the invention comprising a chemiresistor type of sensing component and an external circuit. Here however, the sensing component does not employ a reference. As shown in FIG. 1b, combustible gas sensor 200 just contains metal oxide semiconductor gas sensing element 202 which is shown here in cross section schematic. Sensing element 202 comprises combustion catalyst composition 202a that coats or embeds a pair of electrically conductive terminals 202b and 202c which can be of the fixed-gap or interdigitated type. Terminals 202b, 202c are optionally attached to the surface of inert support 203 and inert support 203 may contain a heating element for heating sensing element 202. Combustion catalyst composition 202a is coated onto terminals 202b, 202c in such a way as to reduce, to the greatest extent possible, the interparticle electrical resistance between the catalyst particles and the electrical contact resistance between the catalyst and the terminals. Coated/embedded terminals 202b, 202c along with optional support 203 are housed within insulated housing 202e with external electrical connectors 202d that are electrically connected to each individual or array of terminals 202b, 202c. Insulated housing 202e is open at 202f such that the gas mixture to be monitored has access to combustion catalyst composition 202a therein. Terminals 202b, 202c are connected, via external electrical connectors 202d, to external electrical circuit 208 which is a measurement circuit which can measure, with precision, the resistivity, conductivity, or capacitance of the combustion catalyst composition 202a that is present between the terminals.

In the present invention, the special low temperature combustion catalyst compositions thus can substitute for conventional combustion catalyst compositions in a chemiresistor sensor circuit. The integration of the inventive humidity-tolerant catalyst composition into the sensor circuit will improve the selectivity of the gas sensor at working temperatures below 200° C.

ChemFET Embodiment

Figure 1C:
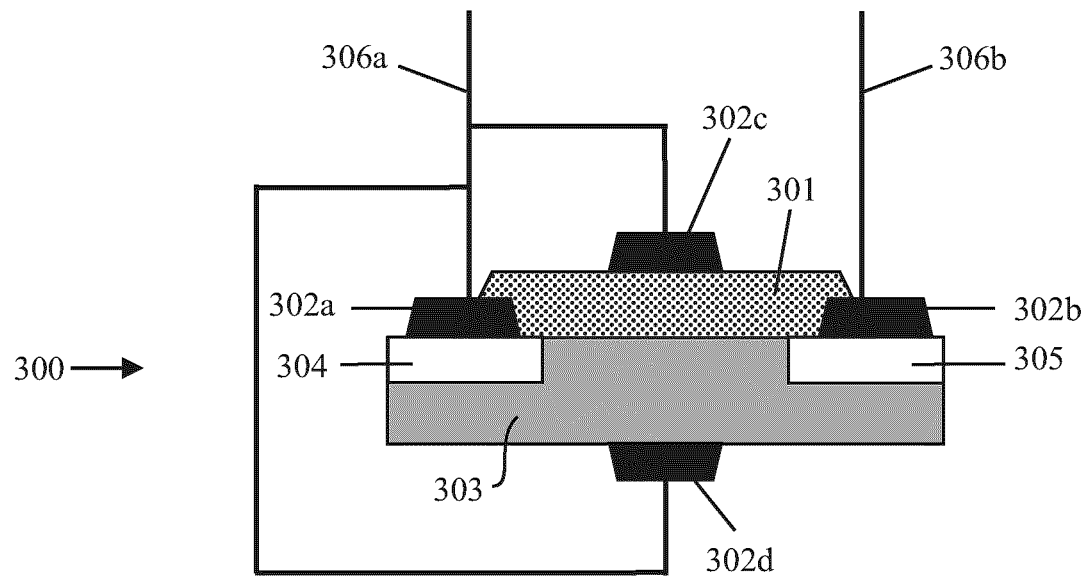
FIG. 1c shows a schematic of a ChemFET type of sensing component for a combustible gas sensor of the invention.

FIG. 1c shows a schematic cross section of a ChemFET sensing component for use in an inventive gas sensor. Here, sensing component 300 is shown without an optional housing and thus the component is exposed to gas from all sides. Sensing component 300 comprises a p-doped semiconductor support 303 into which are integrated two n-doped semiconductor regions, namely source region 304 and drain region 305. The combination of semiconductor support 303 and regions 304, 305 serve as the internal circuit element in this embodiment. Optionally, p-doped support 303 can be mounted to an inert support (not shown) which includes a heater (not shown) for heating the sensor component. Electrodes 303a to 303d are attached and are electrically connected as shown to define source 302a, drain 302b, gate 302c and substrate 302d in this embodiment. ChemFET sensing component 300 also comprises semiconductive combustion catalyst composition 301 which is coated, deposited, or bonded to the surface of the p-type support 303 above the conduction channel that exists between source region 304 and drain region 305.

In this embodiment, the change in the conductivity of the internal circuit element, i.e. semiconductor support 303, is measured between the source and drain terminals using an external electrical circuit (not shown) that measures current. Connectors 306a and 306b serve then as external electrical connectors in sensing component 300 for connection to this external electrical circuit (not shown). To make a current measurement, a voltage potential is provided by the external electrical circuit (not shown) to connectors 306a, 306b and hence across source electrode 302a and drain electrode 302b with only drain electrode 302b being connected to positive potential.

The special low temperature combustion catalyst compositions 301 thus can substitute for conventional combustion catalyst compositions in a ChemFET sensing component. The integration of the inventive humidity-tolerant catalyst composition into the sensor circuit will improve the selectivity of the gas sensor at working temperatures below 200° C.

Gravimetric Embodiment

Figure 1D:
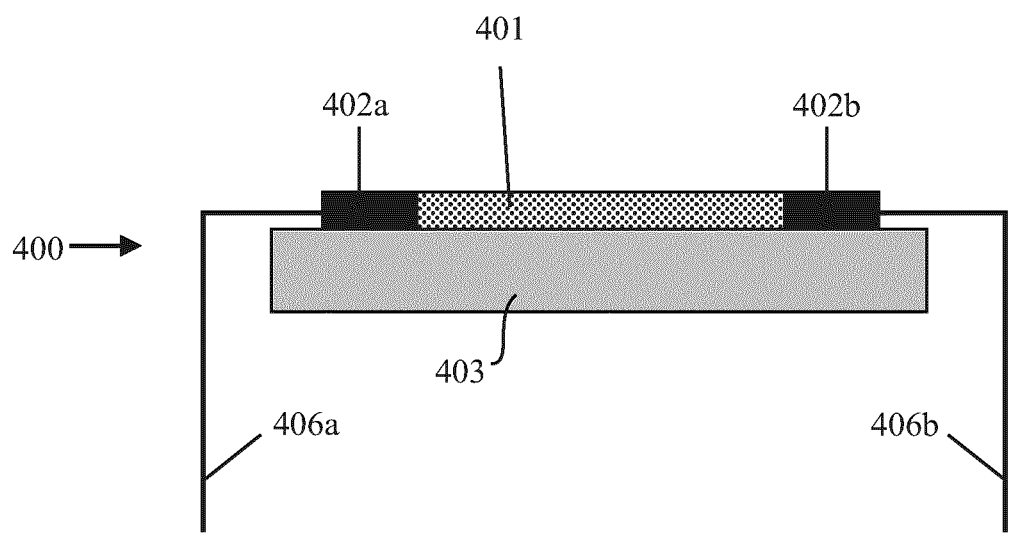
FIG. 1d shows a schematic of a gravimetric type of sensing component for a combustible gas sensor of the invention.

FIG. 1d provides a cross-section schematic of a simplified surface acoustic wave (SAW) sensing component for use in an inventive gas sensor. As in FIG. 1c, sensing component 400 is shown without an optional housing. Combustion catalyst composition 401 is intimately bonded to a section of piezoelectric substrate 403 (such as a quartz crystal). Two terminals 402a and 402b are bonded to the free surface of the piezoelectric substrate on either side of the catalyst coated section of piezoelectric substrate. These terminals will typically be of the interdigitated type. Terminals 402a and 402b are electrically connected to external electrical connectors 406a and 406b respectively which are used to connect to an external electrical circuit (not shown) for measuring the resonant frequency of the piezoelectric substrate.

A variable voltage signal is provided to terminal 402a via external electrical connector 406a to provoke a surface acoustic wave to form in the piezoelectric material. As the wave travels away from terminal 402a, the mass loading on the piezoelectric substrate due to combustion catalyst composition 401 creates an acoustic delay or a variation in the resonant frequency of the oscillating device. This resonant frequency is further perturbed when a combustible gas adsorbs on the surface of the catalyst composition as a precursor to its reaction with the catalyst composition. The resonant frequency of the section of piezoelectric substrate 403 coated with combustion catalyst composition is measured using terminal 402b which, together with suitable transducer circuitry connected to external electrical connector 406b, converts the mechanical oscillations of the oscillator back into electrical impulses. With the use of additional amplification and feedback circuits in the measurement circuit, the resonant frequency of the section of piezoelectric material coated with combustion catalyst composition is continuously monitored.

The special, low temperature combustion catalyst compositions 401 can thus replace a conventional combustion catalyst composition in a gravimetric SAW sensing component. The integration of the inventive humidity-tolerant catalyst composition into the sensor circuit will improve the selectivity of the gas sensor at working temperatures below 200° C.

Pyroelectric Embodiment

Figure 1E:
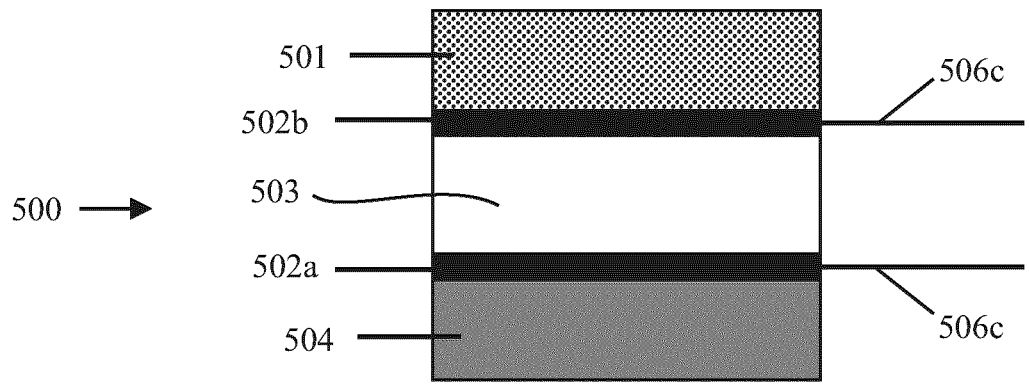
FIG. 1e shows a schematic of a pyroelectric type of sensing component for a combustible gas sensor of the invention.

A schematic of a pyroelectric sensing component for use in an inventive gas sensor is shown in FIG. 1e. Again, sensing component 500 is shown without an optional housing. In FIG. 1e, a thin, crystalline film of pyroelectric material 503 has terminals 502a and 502b bonded to the bottom and top of the pyroelectric film 503 respectively. By necessity, the thickness of the terminals attached, coated, or connected to the surface of the pyroelectric film is minimized to minimize their thermal mass. The surface terminal 502b is coated with a combustion catalyst composition 501 in such a way as to ensure a high degree of thermal communication between terminal 502b and combustion catalyst composition 501. The assembly comprising combustion catalyst composition 501, terminals 502a and 502b, and pyroelectric film 503 can be connected to support 504 to provide mechanical stability. Ideally, support 504 also has minimal thermal mass. Terminals 502a and 502b are electrically connected to external electrical connectors 506c and 506d respectively which are used to connect to an external electrical circuit (not shown) for measuring the transient voltage potential between terminals 502a, 502b.

The special, low temperature combustion catalyst compositions 501 thus can replace a conventional combustion catalyst composition in a pyroelectric sensing component. The integration of the inventive humidity-tolerant catalyst composition into the sensor circuit will improve the selectivity of the gas sensor at working temperatures below 200° C.

Thermoelectric Embodiment

Figure 1F:
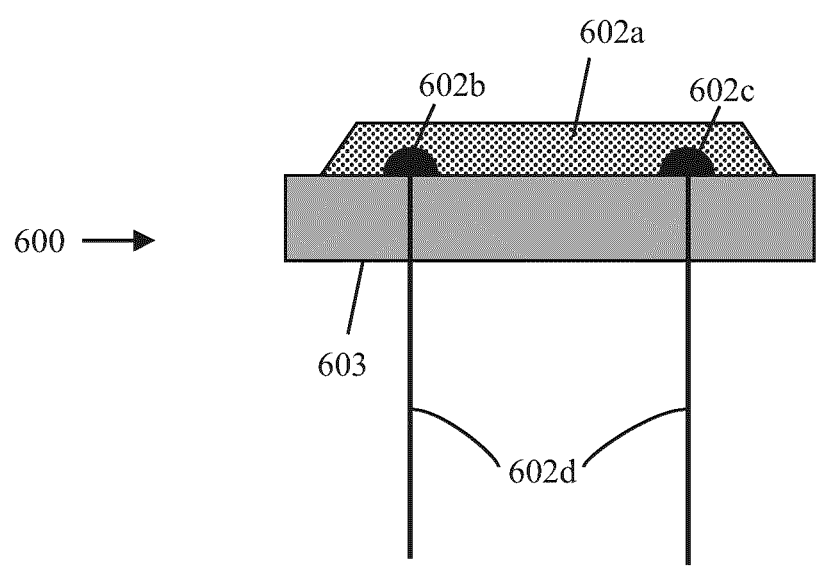
FIG. 1f shows a schematic of a thermoelectric type of sensing component for a combustible gas sensor of the invention.

A schematic for a thermoelectric (or Seebeck effect) sensing component for use in an inventive gas sensor is shown is shown in FIG. 1f. Again, sensing component 600 is shown without an optional housing. In FIG. 1f, terminals 602b and 602c are bonded to inert support 603 that incorporates a heater which generates a temperature gradient between the two terminals. Combustion catalyst composition 602a is deposited onto support 603 and terminals 602b, 602c in such a way as to reduce, to the greatest extent possible, the interparticle electrical resistance between catalyst particles and the electrical contact resistance between the catalyst particles and the terminals. Terminals 602b and 602c are electrically connected to external electrical connectors 602d as shown respectively which are used to connect to an external electrical circuit (not shown) for measuring the voltage potential established between terminals 602b, 602c.

The special, low temperature combustion catalyst compositions 602a thus can replace a conventional combustion catalyst composition in a thermoelectric or Seebeck sensing component. The integration of the inventive humidity-tolerant catalyst composition into the sensor circuit will improve the selectivity of the gas sensor at working temperatures below 20020 C.

At working temperatures below 200° C., fluctuations in the ambient relative humidity can change the catalyst rate constant. These fluctuations can influence the accuracy of the gas sensor because the catalyst rate constant influences the proportionality of the measured property of the sensing component with the concentration of the analyte in air. As previously mentioned, a catalyst rate constant, in general, increases with increasing temperature and decreases with increasing humidity. A range of reaction rates with the catalyst composition is therefore possible for the same analyte concentration at different relative humidity. Sensor systems are therefore considered which can improve the accuracy of gas sensors operating at temperatures below 200° C. and in the presence of humidity. Sensor systems are defined as a combinations of the same or different types of sensors which work together to monitor and correct the measured property of the sensing component for the working conditions of the gas sensor.

At temperatures below 200° C. the water vapour that is present in air can have a measurable influence on the catalyst rate constant for the special catalyst compositions. Since the relative humidity of air is typically variable, gas sensors operating at a fixed working temperature below 200° C. should be calibrated both over a range of analyte concentrations and a range of relative humidity to develop a humidity-corrected sensor response to a range of analyte concentrations in air. Accounting for the influence of humidity on the catalyst rate constant in the calibration will improve the accuracy of the gas sensor.

For applications where the working temperature of the sensor is constant but the relative humidity of the environment can vary it is advantageous to include, in addition to the combustible gas sensor, a relative humidity sensor. Such sensors are known in the art and may include, without limitation, capacitive relative humidity sensors, resistive relative humidity sensors, or thermal conductivity relative humidity sensors. The measurement from a calibrated relative humidity sensor can be combined with the measurement from the combustible gas sensor comprising the special combustion catalyst compositions to determine the humidity-corrected response for the gas sensor. Such a sensor system would improve the accuracy of a gas sensor operating at a fixed working temperature below 200° C.

The special catalyst compositions need not be heated above ambient temperature in order to combust ethylene, for example, and so sensors comprising the special catalyst compositions can be operated at ambient condition and detect ethylene in air. Under such conditions any fluctuation in the ambient temperature will measurably influence the catalyst rate constant. Since both the ambient temperature and the relative humidity of air is typically variable, combustible gas sensors incorporating the special combustion catalyst compositions operating without any external heating should be calibrated over a range of analyte concentrations, relative humidity, and temperature. Ensuring that the calibration takes into account all of the factors that can measurably affect the catalyst rate constant will provide a humidity- and temperature-corrected sensor response to a range of analyte concentrations in air.

For applications where the temperature of the combustible gas sensor incorporating the special combustion catalyst compositions is not constant it would be advantageous to include, in addition to a relative humidity sensor, a temperature sensor to monitor the temperature of the sensing component in the combustible gas sensor. Many temperature sensors are known in the art and include thermocouples, thermistors, resistive temperature detectors (RTD), and non-contact (infrared) temperature detectors. The combined measurements from the gas sensor, relative humidity sensor, and temperature sensor may be used to determine the temperature- and humidity-corrected response of the combustible gas detector comprising the special combustion catalyst composition. Such a sensor system would improve the accuracy of a gas sensor operating under ambient conditions.

It is known that the adsorption of non-analyte gases such as $CO_2$ and water vapour can interfere with the response of a gas sensor; especially for gravimetric sensors where the adsorption of any species on the surface of the combustion catalyst will change its mass and influence the resonant frequency of the oscillator therein. The effect of these non-analyte gases on the sensor response can be at least partially accounted for by incorporating a reference sensor into the sensor system.

A reference sensor would comprise the same elements as the gas sensor but would typically not comprise precious metals. The reference sensor could be used to sense the effect of fluctuating temperature, humidity, and non-analyte gases on the sensing component. The measurement from the reference sensor could be used to adjust the measurement from the combustible gas sensor comprising the special catalyst composition to account for these interferences. Relative humidity and temperature sensors may also be included in the sensor system in addition to the reference sensor. Such a sensor system could improve the accuracy and stability of a combustible gas sensor comprising the special catalyst compositions operating in humid air at temperatures below 200° C.

Pellistor and thermistor sensors inherently incorporate a reference element but other gas sensor types can be considered that may benefit from incorporating a reference element or sensor into a sensor system. A sensor system could be constructed whereby the sensor and reference elements in a thermistor gas sensor are replaced by chemiresistor sensor components. One of the chemiresistor sensor components could comprise the special catalyst compositions while the other could comprise the special catalyst substrate without precious metal. In such a gas sensor system, the reference would at least partially compensate for changes in the resistance of the sensor component as a result of changing temperature, humidity, and non-analyte gases. The voltage potential across the sensor circuit could therefore reflect, to a greater degree, the change in resistance of the sensor component as a result of catalytic combustion of the analyte gas with the special combustion catalyst composition. Additional measurement circuits can be added, as required, to measure the changing property of the sensing component. Relative humidity sensors and temperature sensors could also be incorporated into the sensor system. The combined measurements from the sensor circuit, relative humidity sensor, and temperature sensor may be used to determine the temperature- and humidity-corrected response of the combustible gas sensor comprising the special combustion catalyst composition. Such a sensor system would improve the accuracy of a gas sensor operating at temperatures below 200° C. and in the presence of water vapour.

Gravimetric gas sensors can similarly benefit from the use of a reference sensor in a sensor system. In such a gas sensor system, the reference would at least partially compensate for changes in the resonant frequency of the sensing component as a result of changing temperature, humidity, and non-analyte gases. The signal generated by the sensing component comprising the special combustion catalyst compositions could therefore be corrected for the influence of these variables. The corrected resonant frequency for the sensor component would therefore reflect, to a greater degree, the change in resonant frequency as a result of adsorption of the analyte gas on the special combustion catalyst composition.

Relative humidity sensors and temperature sensors could also be incorporated into the sensor system. The combined measurements from the gas sensor, reference sensor, relative humidity sensor, and temperature sensor may be used to determine the temperature- and humidity-corrected response of the combustible gas sensor comprising the special combustion catalyst composition. Such a sensor system would improve the accuracy of a gas sensor operating at temperatures below 200° C. and in the presence of water vapour.

When it is desirable to measure more than one component in a mixture of combustible gases in humid air, then a sensor system can be considered that takes advantage of the different activation energies for each combustible gas on the special combustion catalyst composition. Each combustible gas in a mixture will have a unique activation energy barrier to overcome before it can react with the special combustion catalyst composition. Because temperature is the most convenient method used to overcome an activation energy barrier, analyte gases can be differentiated by the temperature at which they react with the combustion catalyst composition.

At temperatures below the activation temperature for a combustible gas, catalytic combustion will not take place. Conversely, at sufficiently high temperature a combustion catalyst composition will combust all combustible species regardless of their activation energy. A gas sensor operating at a low temperature may combust only gases with such a low activation temperature while gas sensors operating at a higher temperature will combust gases having such higher activation temperature as well as gases having lower activation temperatures.

In a gas mixture comprising two combustible gases, one gas may have a low activation temperature and the other gas may have a high activation temperature. Detecting the two gas components independently can be accomplished by incorporating a pair of combustible gas sensors into a sensor system whereby each gas sensor operates at a different working temperature. The gas sensor operating at a low working temperature can detect the low activation temperature gas while the gas sensor operating at a higher working temperature will detect both the higher activation temperature and the lower activation temperature gases. The measurement from the lower temperature gas sensor can be used, optionally in conjunction with humidity and temperature sensors, to calculate the concentration of the low temperature activation gas. The measurement values from low temperature gas sensors and, optionally the humidity and temperature sensors, can thus be used to correct, at least in part, the measurement value from the high temperature gas sensor. By using an array of gas sensors that comprise the special combustion catalyst compositions it is possible to simultaneously detect multiple gas species in a mixture by operating a series of gas sensors at different working temperatures.

While the preceding description was directed at certain specific types of gas sensors and arrangements thereof, those skilled in the art will appreciate that alternative embodiments may be contemplated instead.

The following Examples have been included to illustrate certain aspects of the invention but should not be construed as limiting in any way.

EXAMPLES

In these Examples, it is initially demonstrated that relevant combustion catalyst compositions are highly effective for the catalytic combustion of combustible gas, and particularly at low temperature and high relative humidity. Later, in these Examples, it is demonstrated that these combustion catalyst compositions are suitable for use in combustible gas sensors for detecting and measuring the concentration of combustible gases. Finally, the Examples demonstrate the suitability of certain combustion catalyst compositions for the selective measurement of ethylene concentration in a gas mixture comprising other combustible gases.

A series of inventive and comparative catalysts was prepared and tested for catalytic activity toward ethylene combustion at a variety of temperatures and humidity. It was found that the choice of precious metal, co-metal, activation temperature and relative humidity each influenced catalyst activity in a different way. A range of catalysts was discovered that, in aggregate, could address numerous VOC applications from high temperature catalytic combustion to low temperature catalytic combustion at high RH. It was discovered that catalyst compositions containing platinum were active at temperatures below 200° C. in gas streams containing up to 2.3 vol % water vapour (100% RH at 20° C.). It was similarly discovered that catalyst compositions containing palladium were active at low temperature operation (30° C. and below). It was also discovered that the co-metal used along with precious metals altered the behaviour of the catalysts. The activation temperature of the catalyst composition (defined as the pre-treatment temperature of the catalyst material prior to testing) had a pronounced effect on catalyst activity with the platinum formulations preferring high temperature (>500° C.) activations and the palladium compositions preferring to be activated at temperatures below 150° C.

A sodium titanate support was prepared through the hydrothermal treatment of crystalline $TiO_2$. A crystalline nano-scale $TiO_2$ powder (having a mean particle size of around 10 nm) was blended with water to make a slurry. This slurry was then added to a mixture of sodium silicate and sodium hydroxide. The mole ratio of reagents was selected such that the Ti/Si ratio was approximately 10 and the Na/Ti ratio was approximately 1.5. Water was present as an excess reagent and the $H_2O$/Ti mole ratio was over 12. The mixture was homogenized and charged into an autoclave where it was stirred and heated at a temperature between 80 to 110° C. for a period of about 24 hours. The resulting slurry containing the sodium titanate was partially neutralized using acid and then filtered and washed. The resulting filter cake was dried at 60° C. and equilibrated in air before use. The mass of titanate used to prepare a catalyst composition was based on the as-weighed mass of the substrate dried and equilibrated under the specified conditions. No adjustments were made for water adsorbed on the surface of the support.

Catalyst compositions were prepared by adding a selected quantity of sodium titanate to a quantity of water suitable to maintain a suspension when the mixture was stirred. To the agitated slurry was added an aqueous solution containing a precious metal salt and the resulting mixture was stirred for approximately one hour. The amount of metal salt dissolved in solution was calculated such that, after ion exchange, a desired loading of the metal on the titanate would be achieved. For preparations of catalyst compositions containing a co-metal, a second solution containing a transition metal salt was added to the slurry containing the titanate and the resulting mixture was allowed to stir for at least another hour. For compositions containing two or more metals it was necessary to take into account the desired loadings for each metal in the final catalyst composition so that the quantities of metal salts used could be adjusted accordingly. The suspension containing the ion-exchanged titanate was then filtered, washed with deionized water, and dried. The filter cake could be left under ambient conditions overnight to dry or it could be placed in a forced air convection oven at 60° C. Ion exchange was deemed to have been complete when the filtrate was visibly colourless. A series of energy dispersive X-ray spectroscopic measurements (EDX) was performed on the compositions to confirm that the exchange of the metals onto the surface of the sodium titanate was quantitative for the compositions reported herein. The elemental analysis of the various samples suggested the cation exchange capacity CEC of the titanate was between 2 and 3 when the residual sodium ions are taken into consideration.

A catalyst composition containing 5 wt % Pd and 10 wt % Sn was prepared by adding 1.99 g of sodium titanate to 75 mL of water. The mixture was stirred to create a suspension. To this suspension was added a solution of 0.272 g $Pd(NO_3)_2$ dissolved in 30 mL of deionized water. The resulting mixture was stirred for roughly one hour before a solution containing 0.4517 g of $SnCl_2.2H_2O$ dissolved in 30 mL of deionized water was added to the stirred mixture. The bimetallic mixture was then stirred continuously at ambient temperature for an addition hour before the cocoa-coloured suspension was filtered, washed with approximately 200 mL of deionized water, and left under ambient conditions until the filter cake was dry. The catalyst composition prepared in this fashion is referred to here as CC1.

Using these preparation methods a series of catalyst compositions has been prepared which comprise Au, Pt—Zn, Pt—Sn, Pt—Pd—Sn, Pd, Pd—Sn, Pd—Zn, and Pd—Zn—Sn. The quantity of precious and co-metals varied and the platinum loading was varied between 3 and 5 wt %, the palladium loading was varied between 3 and 7 wt %, the tin content was varied between 2 and 10 wt %, the zinc content was varied between 3 and 5 wt %. A gold composition was explored that used a loading of 4 wt % Au. Further combinations and permutations are possible though the compositions provided herein are illustrative of the benefits provided to catalytic combustion systems employing catalysts comprising precious metals supported on an ion-exchangeable titante. A comparative catalyst was purchased from a chemical supplier which comprised Pt supported on $Al_2O_3$. The comparative catalyst consisted of dark grey, 3.2 mm pellets having 1 wt % Pt. The colour of the pellets suggested that the catalyst has already been activated. The comparative catalyst is referred to as Comp. 1.

It is typical for a catalyst composition to be activated before use and the optimal activation conditions are subject to discovery for each catalyst composition. Activation may be used to remove water adsorbed on the surface of the support; the removal of which will leave the metal better exposed for reaction. Such a drying step can take place in any suitable atmosphere. An activation process may be used to decompose metal salts deposited on the surface of the catalyst. Such activation is commonly used after an incipient wetness impregnation where the non-metallic species are oxidized at high temperature and removed as gases or vapours; leaving behind the metal on the support. Such an activation process requires that the gas contain at least some oxidizing agent and so air is frequently selected as an activation gas. Activation can be used to facilitate the surface diffusion of different metal species across the surface of the support; a process which can lead to intimate, electronic interactions between metals. The atmosphere used to promote this interaction is typically air to prevent the reduction of the metals but other atmospheres could be considered depending on the needs of the catalyst and the sensitivities of the metals. Activation can also include a reduction step where a metal is exposed a stream containing a reducing gas. In such cases the activation is used to at least partially reduce the oxidation state of the metal. Whatever the activation process selected for each catalyst composition, the goal in all cases is to maximize the activity of the catalyst. In the present work the activation process for each catalyst composition was carried out in advance of the beds being conditioned in humid air prior to testing.

For catalyst compositions of the present invention a range of activation conditions was necessary to accommodate differences in catalyst chemistry. Samples that required activation temperatures greater than 350° C. were activated in air, ex situ, in a muffle furnace. Catalysts that required activation temperatures less than 350° C. were activated in air, in situ, while connected to the test system. For the platinum catalyst compositions which were heated in air to temperatures greater than 500° C., the samples were heated at 2° C./min to the desired temperature after which the sample was left isothermal for at least 15 hours. For the gold catalyst an activation temperature of 250° C. was used and a stream of pure $H_2$ was passed over the catalyst until the water concentration in the outlet out the bed returned to baseline. For palladium catalyst chemistries it was determined that an activation temperature no greater than 150° C. was optimal as beyond 150° C. the catalyst activity markedly decreased. The heating rate for catalyst compositions activated, in situ, was 5° C./min. Samples activated in situ were typically maintained under isothermal conditions for roughly one hour. The activation conditions described are representative of the conditions used and should not be construed as limiting in any way. To study the comparative catalyst under conditions comparable to the catalysts of the present invention, the Pt—$Al_2O_2$ catalyst (Comp. 1) was activated, in situ, in air at 250° C. before testing.

A test system was constructed for measuring catalyst activity. The test system was capable of delivering a variety of test gases having different compositions and humidity. The test stand was designed in such a way as to allow independent adjustment of the flow rates of dry and wet test gases to achieve, in the bed, a desired RH at a selected test temperature. Simultaneous detection of $H_2O$, $CO_2$, and $C_2H_4$ was accomplished using a mass spectrometer (also called a residual gas analyzer) as a detector. The presence of high concentrations of $N_2$ (m/z=28) in the test gas streams interfered with the trace ethylene signal (m/z=26) and, as a result, a series of measurements—detailed in a following section—was required to address this effect. The $CO_2$ signal was logged at m/z=44 while the water signal was logged at m/z=18.

All catalyst compositions were prepared for testing by using a hydraulic axial press to compress 2 g of binderless powder in a 0.75° ID cylindrical steel die with 5 tons of force. The resulting compressed disc was then crushed and sieved to 20-40 mesh. If the catalyst required high temperature activation (>350° C.) then the 20-40 mesh granules were placed in a crucible and calcined, ex situ, in a muffle furnace otherwise the granules were activated in situ. Typically, approximately 0.5 g of granules were loaded into a straight length of 0.375° outer diameter, 0.305° inner diameter, stainless steel tube connected to the test system using leak-tight compression fittings. The activated catalyst was conditioned using humidified air until the moisture level in the exhaust stream, as measured by a relative humidity sensor, was constant at the desired level. With the bed conditioned, or saturated, at a selected RH, the gas was switched from air to the test gas containing a mixture of 50 ppmv ethylene in air. The total flow rate of the test gas was set to at least 200 sccm until the ethylene signal at the exit of the bed (as measured by the mass spectrometer) was level. This condition ensured that the bed had been fully saturated with ethylene or that "breakthrough" of the ethylene was complete. With ethylene breakthrough complete, the total mass flow rate through the bed was reduced to the measurement flow (typically 25 sccm) and this new flow rate was maintained until the ethylene signal at the exit of the bed was constant. The signal value recorded by the mass spectrometer was averaged over the period of stability and the average value is referred to as the "signal". After this constant ethylene signal was achieved, the humidified test gas was directed to the bypass loop so that the ethylene signal intensity could be measured in the absence of catalyst. When a stable ethylene signal was achieved through the bypass (the "span" signal) the gas flowing through the bypass was switched to humidified, ethylene-free air and the signal at m/z=26 was collected until the signal was stable (the "zero" value). The conversion of ethylene in the test gas was then calculated using the relationship:

$$\text{Conversion } (\%) = (1 - (\text{signal} - \text{zero})/(\text{span} - \text{zero})) \times 100$$

Figure 2:
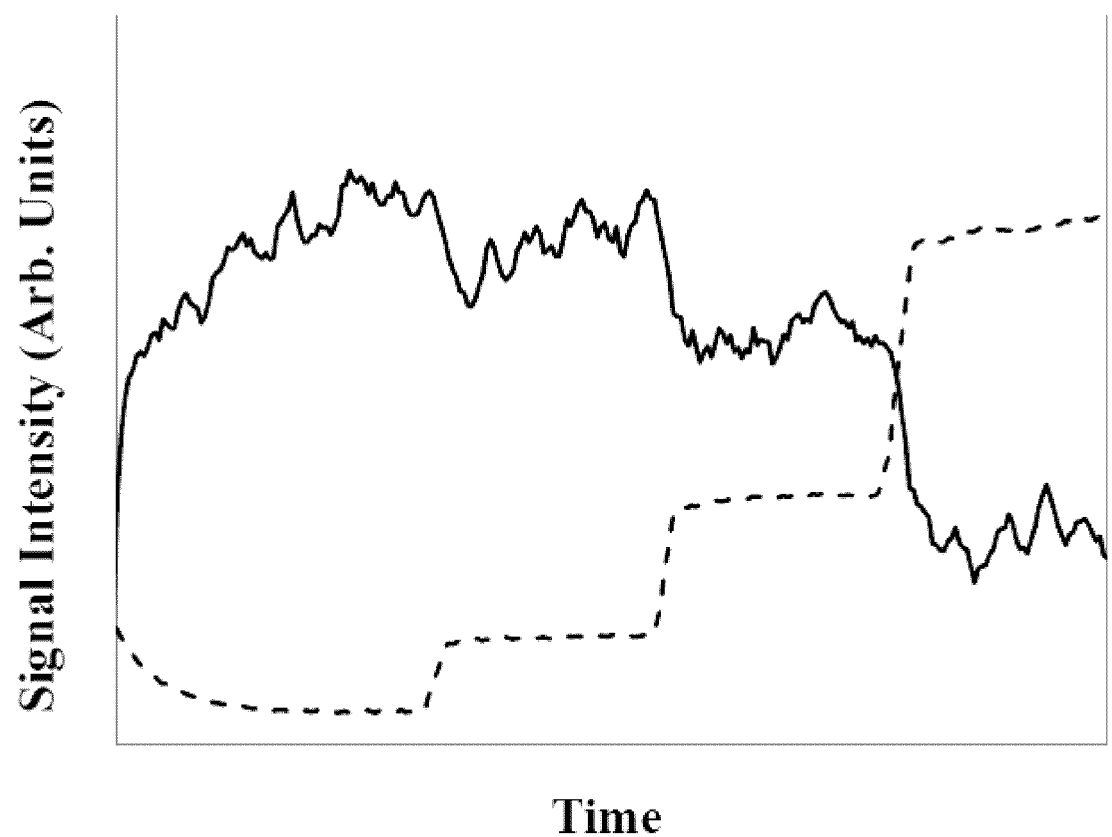
FIG. 2 shows a trace of the mass spectrometer signals for ethylene (solid line) and $CO_2$ (dashed line) as the flow rate of the test gas is sequentially decreased. Time increases from left to right. The flow rate was reduced sequentially from 200 to 100, then to 50, and finally to 25 sccm. The step changes in the $CO_2$ plot indicate when the flow rate was adjusted. CC1 was the catalyst used in the testing.

To establish that a catalyst was combusting ethylene (rather than adsorbing or partially oxidizing the molecule) the products of reaction were measured. The presence of high levels of water vapour in the test gas stream compared to the dilute (50 ppmv) fraction of ethylene renders it impractical to use the water vapour from the combustion of the ethylene as an indicator of catalytic combustion. The signal associated with $CO_2$, however, could be used as a defining indicator of catalytic combustion. The data presented in FIG. 2 relates to a bed that contained 0.443 g of 20-40 mesh granules of the sample catalyst composition CC1. The bed had previously been saturated in air at 20° C. and 35% RH. In the experiment the flow rate of the test gas was changed in order to alter the amount of time the gas spends in contact with the catalyst. The ethylene signal that was measured at the exhaust of the bed decreased in intensity as ethylene was removed from the test gas through catalytic combustion. It can be noted that the signal trace associated with ethylene was highest at a flow rate of 200 sccm. The relatively low degree of conversion at this flow rate was due to the short amount of time that the gas spent in contact with the catalyst. At 25 sccm, however, the extended contact time between the gas stream and catalyst resulted in a higher proportion of the ethylene being converted. While not possible to quantify the signals due to the presence of interfering gases and a lack of an internal standard, the trends in the ethylene data and $CO_2$ data are conclusive with respect to catalytic combustion. As the quantity of ethylene in the product stream of the bed decreased the $CO_2$ level increased concomitantly. These trends only couple when $CO_2$ is a direct product, rather than a side product, of the reaction of ethylene with the catalyst.

Figure 3:
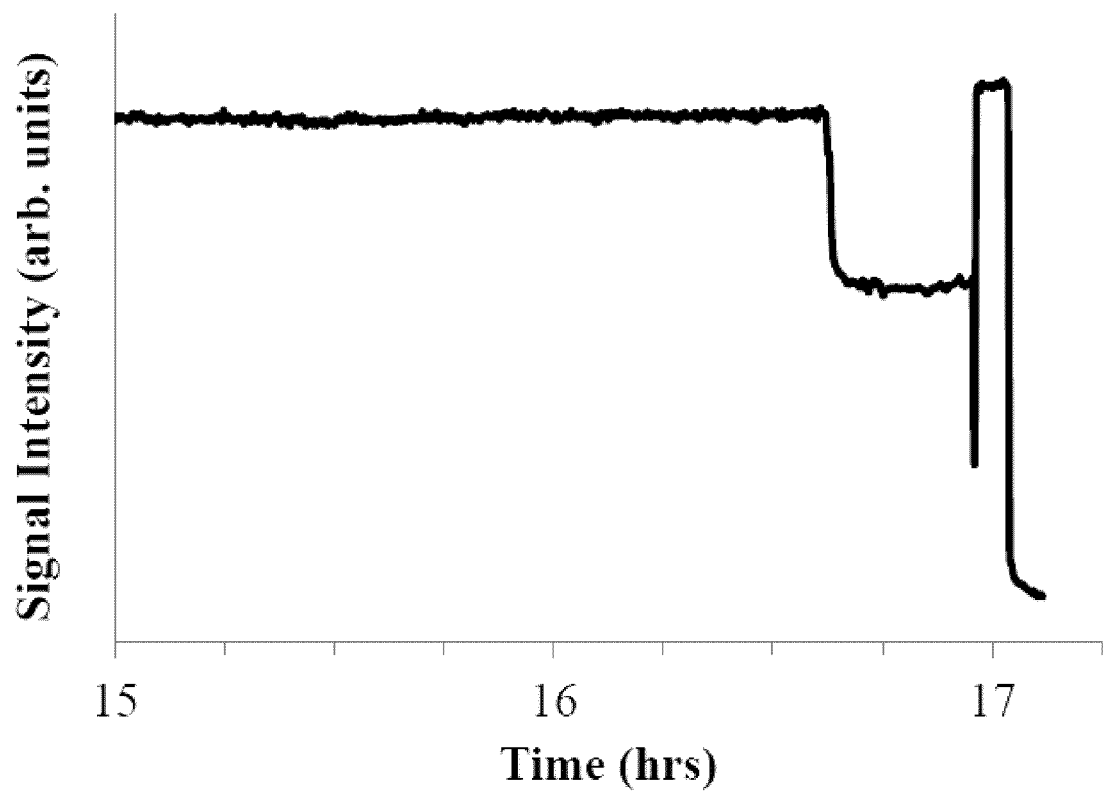
FIG. 3 shows a trace of the mass spectrometer signal for ethylene for a long time-on-stream experiment. After approximately 16.5 hours being exposed to 200 sccm of humidified test gas a sequence of changes in gas flow rate, direction, and composition was used to measure the conversion of ethylene.

The stability of the catalyst in the presence of a water vapour is important toward maintaining catalyst performance in applications where the gas being treated contains a measurable amount of humidity. Artificially high estimates of conversion can be generated if the catalyst bed is not preconditioned, or saturated, with water vapour and/or if the catalyst performance is measured at a short time-on-stream; that is, when relatively few moles of ethylene have been admitted to the catalyst bed relative to the number of moles of precious metal present in the catalyst bed. These criteria are particularly important at low experimental temperatures where water condensation on the surface of the support can be expected to interfere with catalyst function. The plot in FIG. 3 relates to an experiment that used the same bed of CC1 catalyst as in FIG. 2. The bed was again saturated in air at 20° C. and 35% RH after which the catalyst was exposed to a humidified stream of 50 ppmv ethylene in air. For greater than 16 hours the sample was subjected to a 200 sccm flow of the test gas at 20° C. and 35% RH. The catalyst activity was then assessed after approximately 16.5 hours by reducing the flow to 25 sscm. The first step change in the ethylene signal was associated with this change. The decrease in the signal was representative of the greater fraction of ethylene removed at the lower flow rate. Once a stable ethylene signal was achieved (the "signal" value), the flow of humidified test gas was directed to the bypass (at 25 sccm) so that the ethylene signal could be measured in the absence of catalyst. The second step change in the plot was related to this change. Achieving a suitably stable signal through the bypass (the "span" value), the test gas was switched from the test gas to ethylene-free air and the signal was allowed to decay to baseline (the "zero" value). The third step change in the ethylene signal was associated with this change. The obvious difference between the signal and span levels indicated that the catalyst maintained a high degree of conversion after the exposure to a significant quantity of humid ethylene.

The moles of ethylene that passed through the bed during the 16.5 hr exposure represented a molar stoichiometric ratio of 2.7 compared to the moles of palladium present in the bed. Such conditioning ensured that any potential deactivation mechanisms had ample opportunity to manifest and that the activity of the catalyst measured under such conditions should be representative of the steady-state performance of the catalyst. This exceptional catalytic stability in the presence of humidity allows the activity of the catalysts to be reliably assessed at a shorter time on stream (TOS). The TOS is defined as the length of time the catalyst was exposed to the desired flow rate of test gas at (e.g., 25 sccm) before the span and zero measurements were taken. It was deemed that when the ethylene signal in the exhaust of the bed remained unchanged for 30 minutes that the conditions in the bed were deemed to be representative of steady state. For some catalyst compositions shorter equilibration times were used and, as such, some greater degree of uncertainty may be associated with those calculated conversion values. It should be understood that the validity of the conversion values presented herein is greatly enhanced by first pre-conditioning the bed to ensure that the bed is saturated with both water and ethylene before the catalyst activity is measured.

Figure 4:
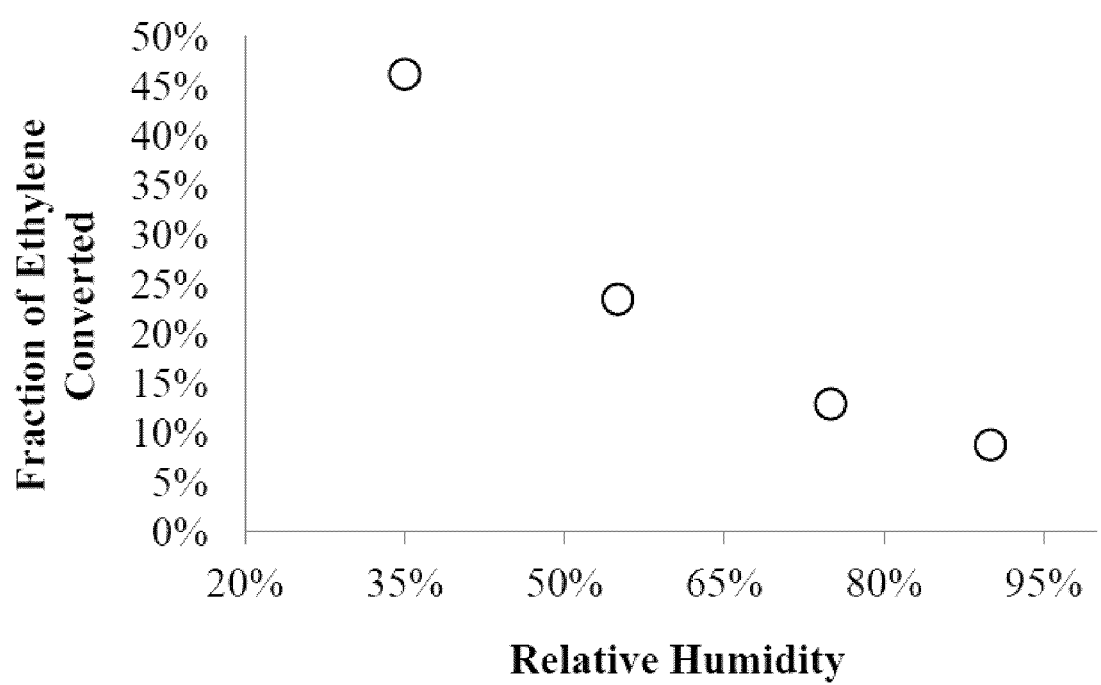
FIG. 4 shows the fraction of ethylene converted in a humidified test feed stream versus relative humidity of the stream at 20° C. for the CC1 catalyst. The flow rate used in all measurements was 25 sccm.

The performance of a catalyst composition over a range of humidity is relevant to applications where either the humidity in the air cannot be reduced or where water vapour is injected into the air to maintain a high relative humidity. FIG. 4 shows the performance of the CC1 catalyst composition over a range of relative humidity at 20° C. For each data point the bed was subjected to the same pre-conditioning procedures involving humidity and ethylene breakthrough outlined previously and the experiments were run sequentially from low to high RH. The influence of humidity is noted on the activity of the catalyst though, even at vapour conditions nearing saturation, the catalyst maintained a measurable portion of the activity it displayed at lower RH.

Additional catalyst compositions were prepared and each unique composition was given a catalyst composition (CC) number. Table 1 specifies the catalyst composition both in terms of the metals supported on the titanate as well as their absolute weight fractions. A prior art catalyst comprised of platinum supported on alumina was obtained and was given the designation Comp 1. The test results for the various catalysts are provided in Table 2 along with the results for the comparative Pt—$Al_2O_3$ catalyst. The sample mass of granules used in the testing is provided in the table as is the activation temperature for that sample. It should be noted that the activation and test conditions can vary for each unique catalyst composition (CC) so named and so the conditions are listed in Table 2. In some cases the same sample of catalyst was used for a number of tests while for other compositions a catalyst bed may have only been used only once. The flow rate of the test gas is specified so that the mass flow of ethylene through the bed used in the measurement of conversion is known. The table also specifies the time-on-stream, or TOS, for the test sequence. The TOS is an approximate number and is used, principally, to differentiate shorter duration testing from longer duration testing. Longer duration tests on beds that have been pre-saturated with water vapour and ethylene provide a strong indication of stable catalytic combustion activity. The relative humidity of the testing is also reported for each test in the table. An RH value appended with an asterisk signifies that the gas stream for that test was brought to the specified level of humidity at 20° C. and so that, for temperatures higher than 20° C., the effective RH in the bed would be lower than that stated in the table. RH values reported without an asterisk are absolute and infer that the RH in the bed was held constant as the temperature of the test was changed. The performance or activity of the catalyst is reported as the fraction of ethylene converted; a value which is reported in separate columns depending on the temperature of the test. Higher values of ethylene conversion per mole of precious metal are generally desirable.

TABLE 1

Catalyst composition number and associated metal composition

| Catalyst Composition Number | Metal Composition |
|---|---|
| CC1 | 5% Pd 10% Sn |
| CC2 | 3% Pd 5% Sn |
| CC3 | 3% Pd 5% Zn |
| CC4 | 5% Pd 6% Zn |
| CC5 | 7% Pd 5% Zn |
| CC6 | 5% Pd 3% Zn 5% Sn |
| CC7 | 4% Pd |
| CC8 | 4% Au |
| CC9 | 3% Pt 2% Sn |
| CC10 | 3% Pt 3% Zn |
| CC11 | 5% Pt 1% Sn |
| CC12 | 2% Pt 2% Pd 2% Sn |
| Comp. 1 | 1% Pt-Al2O3 |

The data in Table 2 demonstrates that palladium-based catalysts can require no activation as they are active at 20° C. directly after ion exchange. It is believed that this observation is unprecedented in the field of combustion catalysis. The observation of intrinsic activity with the palladium catalysts is in contrast to the platinum formulations that strongly benefit from an activation temperature greater than 500° C. The presence of a co-metal appears advantageous as palladium formulations containing tin, zinc, or mixtures of the two all displayed higher degrees of conversion at lower temperatures and higher RH compared to a pure palladium composition. The absolute and relative quantities of the precious metal and co-metals on the titanate appear to influence catalyst performance for the bi-metallic palladium and platinum compositions. Compositions having higher precious metal loadings were capable of converting more ethylene though this effect is confounded by a simultaneous rise in the quantity of co-metal present. In the presence of humidity, particularly above 35% RH, the palladium compositions display higher activity at lower temperatures compared to the platinum compositions while at higher temperatures the platinum-based catalysts displayed greater reactivity per mole of metal compared to the palladium formulations. The gold-loaded titanate catalyst demonstrated an ability to maintain combustion activity in a humid stream from elevated temperatures down to temperatures as low as 20° C. Catalysts containing mixtures of precious metals may be advantageous as indicated by a catalyst comprising Pt, Pd, and Sn which displays a positive response to high temperature activation but also maintains measurable catalyst activity at temperatures as low at 20° C. The comparative catalyst, Comp 1. while appreciably active at 150° C. showed only a fraction of the activity at high temperature compared to all of the inventive catalysts containing platinum (with the exception of the sample of CC11 which had seen no activation).

TABLE 2

Ethylene conversion for inventive and comparative catalyst compositions as a function of composition, temperature, and humidity

| Sample Number | Sample mass (g) | Act. Temp (° C.) | Flow Rate (sccm) | TOS (hrs) | RH | Ethylene Converted (%) Temperature (° C.) | | | | | | | |
|---|---|---|---|---|---|---|---|---|---|---|---|---|---|
| | | | | | | 150 | 100 | 80 | 60 | 40 | 20 | 10 | 5 |
| CC1 | 0.4585 | 20 | 25 | 0.5 | 35% | — | — | — | — | — | 46 | — | — |
| CC1 | 0.4585 | 20 | 25 | 0.5 | 50% | — | — | — | — | — | 35 | 19 | 17 |
| CC1 | 0.4585 | 20 | 25 | 0.5 | 55% | — | — | — | — | — | 23 | — | — |
| CC1 | 0.4585 | 20 | 25 | 0.5 | 75% | — | — | — | — | — | 13 | — | — |
| CC1 | 0.4585 | 20 | 25 | 0.5 | 90% | — | — | — | — | — | 9 | — | — |
| CC1 | 0.4585 | 20 | 25 | 0.5 | 90% | — | — | — | — | — | 7 | 6 | 3 |
| CC2 | 0.4310 | 100 | 25 | 0.2 | 35%* | 100 | 78 | 68 | 39 | 27 | 13 | — | — |
| CC2 | 0.4941 | 100 | 25 | 0.2 | 35% | — | — | — | — | — | 29 | — | — |
| CC2 | 0.4941 | 100 | 25 | 0.2 | 50% | — | — | — | — | — | 8 | — | — |
| CC2 | 0.4941 | 100 | 25 | 0.2 | 75% | — | — | — | — | — | 0 | — | — |
| CC3 | 0.4839 | 100 | 25 | 17 | 35% | — | — | — | — | — | 12 | — | — |
| CC4 | 0.5052 | 150 | 25 | 0.5 | 35% | — | — | — | — | — | 12 | 10 | 10 |
| CC4 | 0.5052 | 150 | 25 | 0.5 | 50% | — | — | — | — | — | 6 | 5 | 9 |
| CC5 | 0.4560 | 20 | 25 | 0.3 | 35% | — | — | — | — | — | 27 | 43 | 44 |
| CC5 | 0.4560 | 20 | 25 | 0.5 | 50% | — | — | — | — | — | 17 | 17 | 18 |
| CC5 | 0.4560 | 150 | 25 | 0.5 | 60% | — | — | — | — | — | 17 | 14 | — |
| CC6 | 0.4417 | 20 | 25 | 0.3 | 10% | — | — | — | — | — | 57 | — | — |
| CC6 | 0.4417 | 20 | 25 | 0.4 | 15% | — | — | — | — | — | 50 | 45 | 38 |
| CC6 | 0.4417 | 20 | 25 | 0.4 | 19% | — | — | — | — | — | — | 59 | — |
| CC6 | 0.4417 | 20 | 25 | 0.2 | 27% | — | — | — | — | — | — | — | 32 |
| CC6 | 0.4417 | 20 | 25 | 0.5 | 50% | — | — | — | — | — | 19 | 15 | 14 |
| CC7 | 0.4040 | 150 | 25 | 0.3 | 35%* | 100 | 92 | 72 | 38 | 9 | 0 | — | — |
| CC8 | 0.4770 | 250 | 25 | 0.4 | 35%* | 89 | 34 | 22 | 8 | 3 | 1 | — | — |
| CC9 | 0.4557 | 600 | 500 | 0.2 | 100%* | 85 | — | — | — | — | — | — | — |
| CC10 | 0.5631 | 600 | 500 | 0.2 | 100%* | 81 | — | — | — | — | — | — | — |
| CC10 | 0.5631 | 600 | 500 | 22 | 100%* | 72 | — | — | — | — | — | — | — |
| CC11 | 0.6488 | 20 | 25 | 0.4 | 100%* | 2 | — | — | — | — | — | — | — |
| CC11 | 0.4692 | 550 | 25 | 0.4 | 100%* | — | 49 | 3 | — | 0 | — | — | — |
| CC11 | 0.4692 | 550 | 500 | 0.5 | 100%* | 94 | — | — | — | — | — | — | — |
| CC12 | 0.4860 | 550 | 25 | 0.5 | 35%* | 100 | 59 | 22 | 11 | 8 | 4 | — | — |
| Comp. 1 | 1.2780 | 250 | 200 | 1.8 | 100%* | 48 | — | — | — | — | — | — | — |

The results provided in Table 2 demonstrate the range of capabilities of the titanate-based combustion catalyst compositions. Through the selection of a precious metal, an optional co-metal, and developing the correct activation conditions a catalyst composition can be tuned to function at high or low temperature and at lower or higher humidity. Some catalyst compositions of the present invention are significantly more active at high temperature under fully-humidified gas compared to a prior art catalyst, while other catalyst compositions demonstrate unparalleled activity under refrigerated temperatures and at near-saturated humidity. The versatility of the combustion catalysts of the present invention allows them to address the greatest array of applications that require trace VOC contaminant removal from air.

The preceding Examples demonstrate that relevant combustion catalyst compositions are highly effective for the catalytic combustion of combustible gas, and particularly at low temperature and high relative humidity.

Later, a test system was constructed to measure the catalyst rate constants of the aforementioned combustion catalyst compositions in the presence of the full complement of gases and vapours produced by ethylene-producing perishables. By challenging these combustion catalyst compositions with a complex mixture of organic species, it is possible to determine both their efficiency and selectivity under conditions representative of postharvest applications. The test system was constructed in such a way as to be able to characterize the catalyst rate constant and catalyst selectivity as a function of temperature and relative humidity.

A hermetically sealed vessel containing a quantity of fruit was fluidly coupled to an empty tank (which served as an accumulator) via an inlet and return line. Shut-off valves were present in the inlet and return lines of the vessel containing the fruit so that the fruit could be isolated from the accumulator once a desired quantity of ethylene (and associated headspace gases) was produced. A resealable port was installed in the fruit vessel to allow other trace gases—not naturally produced by the fruit—to be injected into the test system. Through this port, a small amount of ethane gas was injected into the system via a gas-tight syringe. Ambient air comprises a small amount of methane (circa 2 ppm) and so methane was also present as an analyte in the test gas. A temperature and relative humidity sensor was fluidly coupled in-line with the accumulator to continuously monitor the relative humidity of the recirculating gas. The entire test system (with the exception of a gas chromatograph as per below) was integrated into an insulated enclosure which could be refrigerated to temperatures below 22° C. A gas-tight diaphragm pump was used to continuously circulate the atmosphere in the test system.

As part of its natural respiration cycle, the fruit contained in the fruit vessel produced ethylene, $CO_2$, and trace amounts of other organic compounds associated with the perishable such as alcohols, aldehydes, keytones, or acetates. Banana, for example, in addition to producing ethylene, $CO_2$, and water vapour produces quantities of isoamyl acetate which gives the fruit its distinctive odour. As a result, the atmosphere in the test system comprised not just ethylene and water vapour but the full complement of organic compounds co-produced by the perishable.

The recirculation system was fluidly coupled to the sampling loop of a gas chromatograph (GC). By incorporating the GC sample loop into the recirculation system, the concentration of ethylene and other detectable species in the system could be automatically sampled and monitored over time. The GC was equipped with a flame ionization detector and was able to accurately detect light alkanes such as methane, ethane, and ethylene at concentrations as low as 0.1 ppm. The concentrations of the co-produced organic species could not be resolved on the GC due to technical limitations of the equipment, but their presence was unmistakable as evidenced by the odour that accompanied the test gas when it was vented to atmosphere at the end of an experiment.

To accumulate ethylene and associated co-produced organic compounds in the test system, the atmosphere surrounding the fruit was recirculated between the fruit vessel and the accumulator at a rate to ensure that the atmosphere throughout the test system was homogenous. While ethylene and other co-produced gases and vapours were being accumulated, the recirculation of the gas was directed through a bypass line so as not to alter the composition of the gases produced by the perishable. The atmosphere in the test system was recirculated between the fruit chamber and accumulator, via the bypass line, the relative humidity sensor, and the GC sample loop until a desired ethylene concentration and relative humidity was reached. Once the desired atmosphere was reached, the fruit chamber was fluidly isolated from the accumulator, and the atmosphere in the accumulator was continually recycled via the bypass line, the relative humidity sensor, and the GC sample loop. Once isolated, the gas concentrations in the accumulator were fixed and the measured analyte concentrations and relative humidity were constant as a function of time.

A bed containing granular combustion catalyst composition (as indicated below) was fluidly coupled in parallel to the bypass line by a series of shut off valves so that the recirculating gas could be drawn either through the bypass line or through the combustion catalyst composition bed. When the concentration of ethylene in the accumulator was determined to be constant, the atmosphere in the accumulator was then directed to be recirculated through the combustion catalyst composition bed. Because the gas in the accumulator was recirculated through the combustion catalyst composition bed and monitored via the GC sample loop, any change in the concentration of the analytes (as measured by the GC) in the tank was due to their reaction with the combustion catalyst composition.

Figure 5:
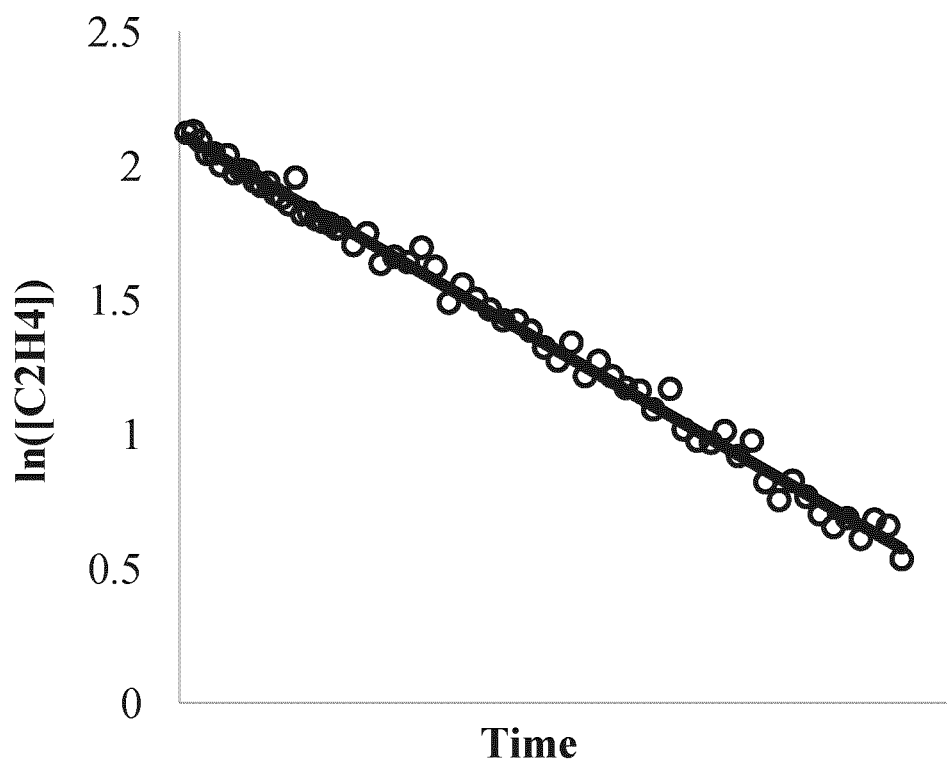
FIG. 5 shows a plot of the concentration of ethylene in an accumulator as a function of time during testing of exemplary catalyst CC1 at 22° C. and ~85% RH.

FIG. 5 shows a plot of the concentration of ethylene in the accumulator as a function of time for catalyst composition CC1 at 22° C. and ~85% RH. The concentration of ethylene is reported as the natural logarithm of the measured ethylene concentration. The open circles represent the measured data points, while the solid line represents a linear, least-squares fit to the data. The ethylene in the batch reactor was collected from a quantity of bananas.

The data shows that throughout a 4 times drop in concentration of ethylene, the trend of the natural logarithm of the ethylene concentration is linear with respect to time. This result, as it is known in the art, establishes that the catalytic reaction is first order with respect to ethylene. A catalyst that has a first order reaction with respect to an analyte is ideal for sensor applications because the response of the sensor circuit will be directly proportional to the ethylene concentration over a wide range of concentrations. The data also demonstrates that the reactivity of the catalyst composition is not reduced as the concentration of ethylene is reduced. This result indicates that the catalyst has a high reactivity toward ethylene, because it is capable of combusting ethylene at concentrations approaching zero. The data in FIG. 5 establishes that a sensor operating at room temperature and incorporating catalyst composition CC1 would be expected to be able to detect ethylene in almost fully humid air at concentrations below 1 ppm.

Figure 6:
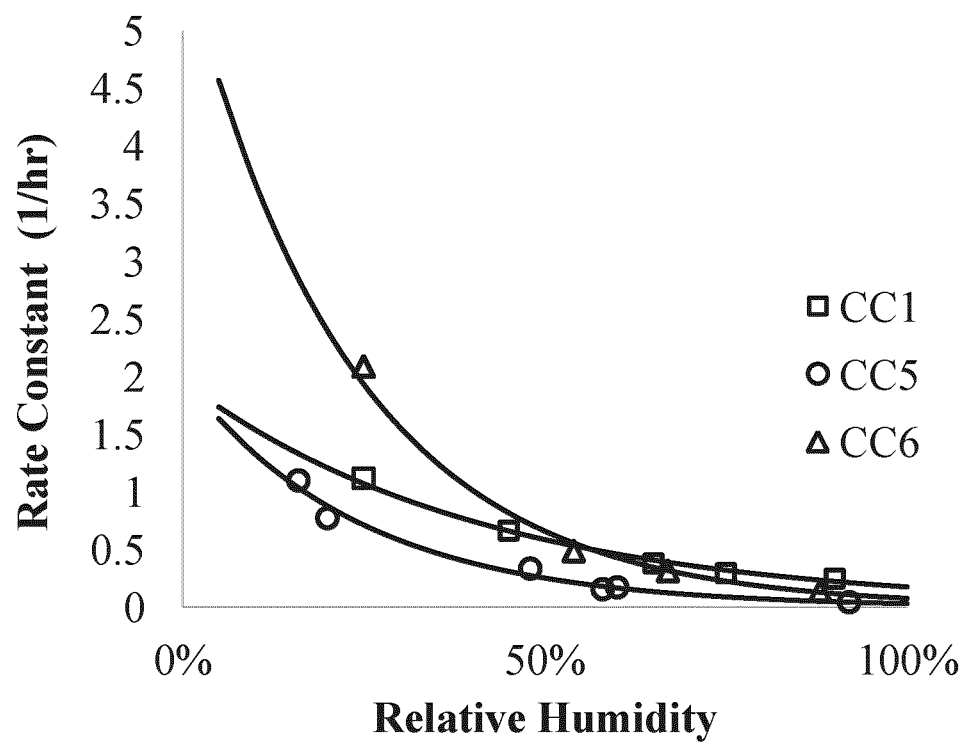
FIG. 6 shows the trend of the catalyst rate constant as a function of RH for during testing of exemplary catalysts CC1, CC5, and CC6 at 22° C.

FIG. 6 shows the trend of the catalyst rate constant as a function of RH for catalyst compositions CC1, CC5, and CC6 at 22° C. In all cases, the catalyst rate constant follows an inverse relationship with respect to relative humidity where higher reaction rate constants are measured at lower relative humidity. While each formulation follows a unique trend, all catalyst compositions manifest a predictable, exponential dependence on the relative humidity. The data in FIG. 6 shows the influence of the relative humidity on the reaction rate constant of the catalyst, and therefore this should be taken into consideration for sensors operating at temperatures below 200° C.

Figure 7:
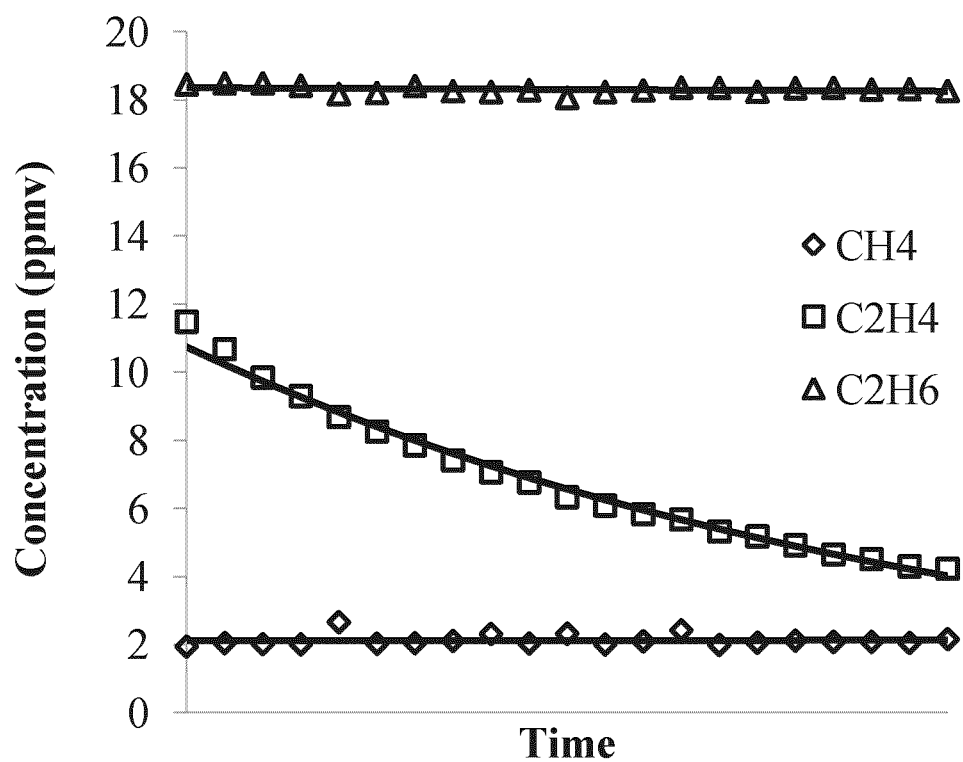
FIG. 7 shows the concentration of methane, ethane, and ethylene as a function of time during testing of exemplary catalyst CC6 at 22° C. and ~30% RH.

FIG. 7 shows the concentration of methane, ethane, and ethylene as a function of time for catalyst composition CC6 at 22° C. and ~30% RH. The methane is present as a natural component in air at a concentration of roughly 2 ppmv. The ethane was injected as a tracer gas via the resealable port built into the fruit vessel. The ethylene (and associated co-produced organic compounds) was accumulated from a quantity of avocado. It is apparent from the data in FIG. 7 that only the concentration of ethylene decreases as a function of time. These results demonstrate that the operation of this combustion catalyst composition at low temperature can be used to enhance the selectivity of a gas sensor because the combustion catalyst composition is suitably stable toward significant levels of humidity.

The above Examples therefore demonstrate that relevant combustion catalyst compositions are suitable for use in combustible gas sensors for detecting and measuring the concentration of combustible gases. Further, the suitability of certain combustion catalyst compositions was demonstrated for the selective measurement of ethylene concentration in a gas mixture comprising other combustible gases.

All of the above U.S. patents, U.S. patent applications, foreign patents, foreign patent applications and non-patent publications referred to in this specification, are incorporated herein by reference in their entirety.

While particular elements, embodiments and applications of the present invention have been shown and described, it will be understood, of course, that the invention is not limited thereto since modifications may be made by those skilled in the art without departing from the spirit and scope of the present disclosure, particularly in light of the foregoing teachings. Such modifications are to be considered within the purview and scope of the claims appended hereto.

The invention claimed is:

1. A combustible gas sensor for detecting a combustible gas in a gas mixture comprising:
   a sensing component comprising:
      a combustion catalyst composition comprising an amount of a precious metal supported on an ion-exchangeable alkali metal titanate substrate, and wherein the combustion catalyst composition is exposed to the gas mixture;
      an internal circuit element in intimate contact with the combustion catalyst composition; and
      external electrical connectors electrically connected to the internal circuit element; and
   an electrical circuit connected to the external electrical connectors for measuring a property of the sensing component.

2. The combustible gas sensor of claim 1 wherein the alkali metal titanate is sodium titanate.

3. The combustible gas sensor of claim 1 wherein the precious metal is selected from the group consisting of platinum, palladium, gold and silver.

4. The combustible gas sensor of claim 1 comprising an amount of an additional precious metal supported on the ion-exchangeable alkali metal titanate substrate.

5. The combustible gas sensor of claim 1 comprising an amount of an additional transition metal on the ion-exchangeable alkali metal titanate substrate.

6. The combustible gas sensor of claim 5 wherein the additional transition metal is zinc, tin, or cobalt.

7. The combustible gas sensor of claim 3 wherein the combustion catalyst composition comprises Pt, Pt-Zn, Pt-Sn, Au, Pt-Pd-Sn, Pd, Pd-Zn, Pd-Sn, or Pd-Zn-Sn.

8. The combustible gas sensor of claim 1 wherein the internal circuit element is a resistance wire, a thermistor, a pair of terminals, a field effect transistor, an electromechanical oscillator, or a pyroelectric crystal.

9. The combustible gas sensor of claim 1 wherein the measured property is a property of the combustion catalyst composition or the internal circuit element.

10. The combustible gas sensor of claim 1 wherein the measured property is the resistance across the sensing component, the capacitance of the sensing component, the conductance of the sensing component, the harmonic frequency of the sensing component, the voltage across the sensing component, or the current flow through the sensing component.

11. A method for detecting a combustible gas in a gas mixture comprising oxygen, the method comprising:
   obtaining the combustible gas sensor of claim 1;
   exposing the combustion catalyst composition in the sensing component to the gas mixture; and
   measuring the property of the sensing component.

12. The method of claim 11 wherein the combustible gas is ethylene, formaldehyde, or carbon monoxide.

13. The method of claim 11 wherein the gas mixture comprises water vapour and the method comprises exposing the combustion catalyst composition in the sensing component to the gas mixture at a temperature below 200° C. and at a relative humidity above 0.5%.

14. The method of claim 11 comprising determining the concentration of the combustible gas from the measured property of the sensing component.

15. A method for selectively measuring the concentration of ethylene in a gas mixture comprising ethylene and oxygen, the method comprising:
   obtaining the combustible gas sensor of claim 1;
   exposing the combustion catalyst composition in the sensing component to the gas mixture; and
   measuring the property of the sensing component.

16. The method of claim 15 wherein the gas mixture comprises water vapour and the method comprises exposing the combustion catalyst composition in the sensing component to the gas mixture at a temperature below 200° C. and at a relative humidity above 0.5%.

17. The method of claim 15 wherein the gas mixture comprises methane and ethane.

* * * * *